(12) United States Patent
Lin et al.

(10) Patent No.: US 9,931,379 B2
(45) Date of Patent: Apr. 3, 2018

(54) OXYNTOMODULIN ANALOGS AND METHODS OF MAKING AND USING SAME

(71) Applicants: The Research Foundation for The State University of New York, Buffalo, NY (US); California Institute for Biomedical Research, La Jolla, CA (US)

(72) Inventors: Qing Lin, Getzville, NY (US); Avinash Muppidi, San Diego, CA (US); Weijun Shen, San Diego, CA (US); Huafei Zou, San Diego, CA (US); Peter Schultz, La Jolla, CA (US); Yulin Tian, Amherst, NY (US)

(73) Assignees: The Research Foundation for The State University of New York, Buffalo, NY (US); California Institute for Biomedical Research, La Jolla, CA (US)

( * ) Notice: Subject to any disclaimer, the term of this patent is extended or adjusted under 35 U.S.C. 154(b) by 0 days.

(21) Appl. No.: 15/451,503

(22) Filed: Mar. 7, 2017

(65) Prior Publication Data
US 2017/0196940 A1 Jul. 13, 2017

Related U.S. Application Data

(63) Continuation of application No. PCT/US2016/059705, filed on Oct. 31, 2016.

(60) Provisional application No. 62/248,866, filed on Oct. 30, 2015.

(51) Int. Cl.
*A61K 38/26* (2006.01)
*C07K 14/605* (2006.01)

(52) U.S. Cl.
CPC ............ *A61K 38/26* (2013.01); *C07K 14/605* (2013.01)

(58) Field of Classification Search
CPC ...... A61K 38/22; A61K 38/26; C07K 14/575; C07K 14/605
See application file for complete search history.

(56) References Cited

U.S. PATENT DOCUMENTS

2011/0183902 A1* 7/2011 Sinha Roy ........... C07K 14/575
514/6.9
2014/0057857 A1* 2/2014 Lin ...................... C07K 1/1077
514/21.1

FOREIGN PATENT DOCUMENTS

CN          104610444 A  *  5/2015
WO    WO-2015095406 A1  *  6/2015 ........... A61K 9/0019

* cited by examiner

*Primary Examiner* — Jeffrey E. Russel
(74) *Attorney, Agent, or Firm* — Hodgson Russ LLP

(57) ABSTRACT

Provided are oxyntomodulin analogs. The peptide analogs have at least two cysteines. The two cysteines are separated by six amino acids such that they can be crosslinked using suitable crosslinking moieties. The crosslinked peptides have long half-lives and/or efficacy. For example, peptide analog compositions are used for inducing weight loss and/or reducing blood glucose levels.

12 Claims, 7 Drawing Sheets

SEQUENCE LISTING

<160> NUMBER OF SEQ ID NOS: 18

<210> SEQ ID NO 1

```
<211> LENGTH: 37
<212> TYPE: PRT
<213> ORGANISM: artificial sequence
<220> FEATURE:
<223> OTHER INFORMATION: Synthetic peptide

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 2
<211> LENGTH: 15
<212> TYPE: PRT
<213> ORGANISM: artificial sequence
<220> FEATURE:
<223> OTHER INFORMATION: Synthetic peptide

<400> SEQUENCE: 2

His Ser Gln Gly Thr Phe Thr Ser Asp Tyr Ser Lys Tyr Leu Asp
1               5                   10                  15

<210> SEQ ID NO 3
<211> LENGTH: 6
<212> TYPE: PRT
<213> ORGANISM: artificial sequence
<220> FEATURE:
<223> OTHER INFORMATION: Synthetic peptide

<400> SEQUENCE: 3

Arg Ala Gln Asp Phe Val
1               5

<210> SEQ ID NO 4
<211> LENGTH: 6
<212> TYPE: PRT
<213> ORGANISM: artificial sequence
<220> FEATURE:
<223> OTHER INFORMATION: Synthetic peptide

<400> SEQUENCE: 4

Ala Ala Lys Glu Phe Ile
1               5

<210> SEQ ID NO 5
<211> LENGTH: 6
<212> TYPE: PRT
<213> ORGANISM: artificial sequence
<220> FEATURE:
<223> OTHER INFORMATION: Synthetic peptide

<400> SEQUENCE: 5

Ala Val Arg Leu Phe Ile
1               5

<210> SEQ ID NO 6
<211> LENGTH: 13
<212> TYPE: PRT
<213> ORGANISM: artificial sequence
<220> FEATURE:
<223> OTHER INFORMATION: Synthetic peptide

<400> SEQUENCE: 6
```

Trp Leu Met Asn Thr Lys Arg Asn Arg Asn Asn Ile Ala
1               5                   10

<210> SEQ ID NO 7
<211> LENGTH: 20
<212> TYPE: PRT
<213> ORGANISM: artificial sequence
<220> FEATURE:
<223> OTHER INFORMATION: Synthetic peptide

<400> SEQUENCE: 7

His Ser Gln Gly Thr Phe Thr Ser Asp Tyr Ser Lys Tyr Leu Asp Ser
1               5                   10                  15

Arg Arg Ala Gln
            20

<210> SEQ ID NO 8
<211> LENGTH: 6
<212> TYPE: PRT
<213> ORGANISM: artificial sequence
<220> FEATURE:
<223> OTHER INFORMATION: Synthetic peptide

<400> SEQUENCE: 8

Phe Val Gln Trp Leu Met
1               5

<210> SEQ ID NO 9
<211> LENGTH: 8
<212> TYPE: PRT
<213> ORGANISM: Synthetic Peptide

<400> SEQUENCE: 9

Lys Arg Asn Arg Asn Asn Ile Ala
1               5

<210> SEQ ID NO 10
<211> LENGTH: 29
<212> TYPE: PRT
<213> ORGANISM: artificial sequence
<220> FEATURE:
<223> OTHER INFORMATION: Synthetic peptide

<400> SEQUENCE: 10

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 11
<211> LENGTH: 37
<212> TYPE: PRT
<213> ORGANISM: artificial sequence
<220> FEATURE:
<223> OTHER INFORMATION: Synthetic peptide

<400> SEQUENCE: 11

His Ser Gln Gly Thr Phe Thr Ser Asp Tyr Ser Lys Tyr Leu Asp Glu
1               5                   10                  15

Cys Ala Ala Lys Glu Phe Ile Cys Trp Leu Met Asn Thr Lys Arg Asn
            20                  25                  30

Arg Asn Asn Ile Ala
        35

```
<210> SEQ ID NO 12
<211> LENGTH: 37
<212> TYPE: PRT
<213> ORGANISM: artificial sequence
<220> FEATURE:
<223> OTHER INFORMATION: Synthetic peptide

<400> SEQUENCE: 12

His Ser Gln Gly Thr Phe Thr Ser Asp Tyr Ser Lys Tyr Leu Asp Ser
1               5                   10                  15

Cys Arg Ala Gln Asp Phe Val Cys Trp Leu Met Asn Thr Lys Arg Asn
            20                  25                  30

Arg Asn Asn Ile Ala
        35

<210> SEQ ID NO 13
<211> LENGTH: 37
<212> TYPE: PRT
<213> ORGANISM: artificial sequence
<220> FEATURE:
<223> OTHER INFORMATION: Synthetic peptide

<400> SEQUENCE: 13

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Met Cys Thr Lys Arg Asn
            20                  25                  30

Arg Asn Asn Ile Ala
        35

<210> SEQ ID NO 14
<211> LENGTH: 37
<212> TYPE: PRT
<213> ORGANISM: artificial sequence
<220> FEATURE:
<223> OTHER INFORMATION: Synthetic peptide

<400> SEQUENCE: 14

His Ser Gln Gly Thr Phe Thr Ser Asp Tyr Ser Lys Tyr Leu Asp Glu
1               5                   10                  15

Cys Arg Ala Gln Asp Phe Val Cys Trp Leu Met Asn Thr Lys Arg Asn
            20                  25                  30

Arg Asn Asn Ile Ala
        35

<210> SEQ ID NO 15
<211> LENGTH: 37
<212> TYPE: PRT
<213> ORGANISM: artificial sequence
<220> FEATURE:
<223> OTHER INFORMATION: Synthetic peptide

<400> SEQUENCE: 15

His Ser Gln Gly Thr Phe Thr Ser Asp Tyr Ser Lys Tyr Leu Asp Glu
1               5                   10                  15

Cys Ala Val Arg Leu Phe Ile Cys Trp Leu Met Asn Thr Lys Arg Asn
            20                  25                  30

Arg Asn Asn Ile Ala
        35

<210> SEQ ID NO 16
<211> LENGTH: 9
<212> TYPE: PRT
```

```
<213> ORGANISM: artificial sequence
<220> FEATURE:
<223> OTHER INFORMATION: Synthetic peptide

<400> SEQUENCE: 16

Thr Lys Arg Asn Arg Asn Asn Ile Ala
1               5

<210> SEQ ID NO 17
<211> LENGTH: 30
<212> TYPE: PRT
<213> ORGANISM: human

<400> SEQUENCE: 17

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 18
<211> LENGTH: 38
<212> TYPE: PRT
<213> ORGANISM: human

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
            35
```

OXYNTOMODULIN ANALOGS AND METHODS OF MAKING AND USING SAME

CROSS REFERENCE TO RELATED APPLICATIONS

This application is a continuation of International Patent Application No. PCT/US2016/059705, filed on Oct. 31, 2016, which claims priority to U.S. Provisional Application No. 62/248,866, filed on Oct. 30, 2015, the disclosures of each of which are hereby incorporated by reference.

STATEMENT REGARDING FEDERALLY SPONSORED RESEARCH

This invention was made with government support under contract no. GM085092 awarded by the National Institutes of Health. The government has certain rights in the invention.

FIELD OF THE DISCLOSURE

The disclosure generally relates to oxyntomodulin analogs. More particularly the disclosure relates to crosslinked oxyntomodulin analogs and use thereof.

BACKGROUND OF THE DISCLOSURE

Obesity is a major risk factor for developing type 2 diabetes mellitus (T2DM). Oxyntomodulin (OXM), a 37-amino acid peptide hormone derived from proglucagon, is an attractive potential therapy for treatment of T2DM due to its multifaceted effects on glucose homeostasis, food intake and energy expenditure. Remarkably, the weight loss and glucose lowering effects of OXM were found to be superior to those of the glucagon-like peptide-1 (GLP-1) receptor only agonists after infusion in preclinical models. However, the clinical application of OXM is limited by its short circulatory half-life; hence, PEG and lipid modified OXM analogs have been explored. While these conjugates have shown significantly longer circulatory half-lives, they often exhibit considerably reduced potency; as a result, relatively large quantities of the modified peptides are injected during their administration. These large doses have limited the exploration of alternative delivery technologies such as microneedles or nanoparticles.

SUMMARY OF THE DISCLOSURE

The present disclosure provides OXM analogs that exhibit increased plasma stability and higher potency in activating both GLP-1R and GCGR (See Tables 1 and 2). OXM analogs include, but are not limited to, crosslinked analogs.

For example, OXM analogs are crosslinked peptides having the following sequence: HSQGTFTSDYSKYLDSR-RAQDFVQWLMNTKRNRNNIA (SEQ ID NO:1), or variants thereof having at least 65% homology with SEQ ID NO:1. The first amino acid at position i and the second amino acid at position i+7 are replaced independently by L-cysteine or D-cysteine of SEQ ID NO:1. Position i can be at any position from and including number 7 to number 30. The analog is crosslinked with a crosslinking moiety between the cysteines at i and i+7. The crosslinking moiety is selected from the group consisting of:

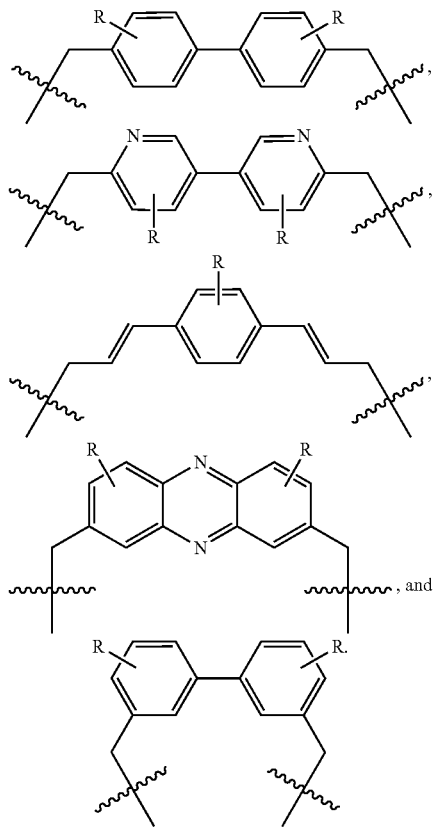

The substituent R at each occurrence is independently an H, a polyethylene glycol (PEG) group, a lipid group, or fatty diacid group that can be separated from the crosslinking moiety by a spacer moiety (e.g., a flexible spacer moiety such as, for example, a PEG spacer moiety).

The crosslinked OXM analogs have extended half-life and/or exhibit superior anti-hyperglycemic activity compared to wild-type OXM.

The present disclosure also provides methods of treating diabetes, including type 2 diabetes mellitus, by administration to a subject of one or more of the crosslinked OXM analogs of the present disclosure. The disclosure also provides methods of lowering the blood glucose levels of a subject by administration to the subject one of or more of the crosslinked OXM analogs. The present disclosure also provides methods of inducing weight loss in a subject by administration to the subject one or more of the crosslinked OXM analogs.

BRIEF DESCRIPTION OF THE FIGURES

For a fuller understanding of the nature and objects of the disclosure, reference should be made to the following detailed description taken in conjunction with the accompanying figures.

The oxyntomodulin structure was modeled after the crystal structure of glucagon (PDB code: 1GCN) with the octapeptide extension shown as a dotted type II β-helical turn.

Figure 2:
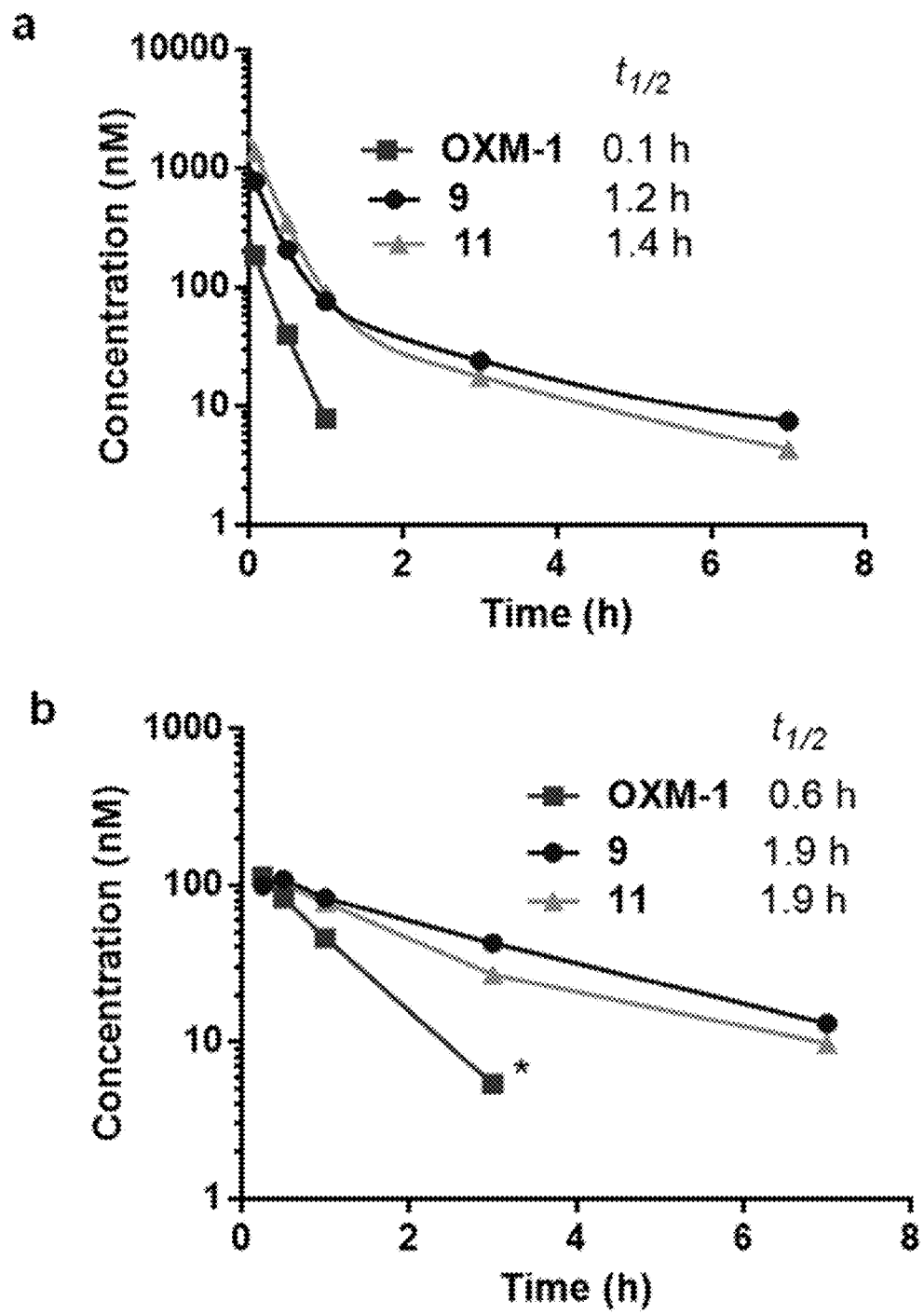
Figure 2:
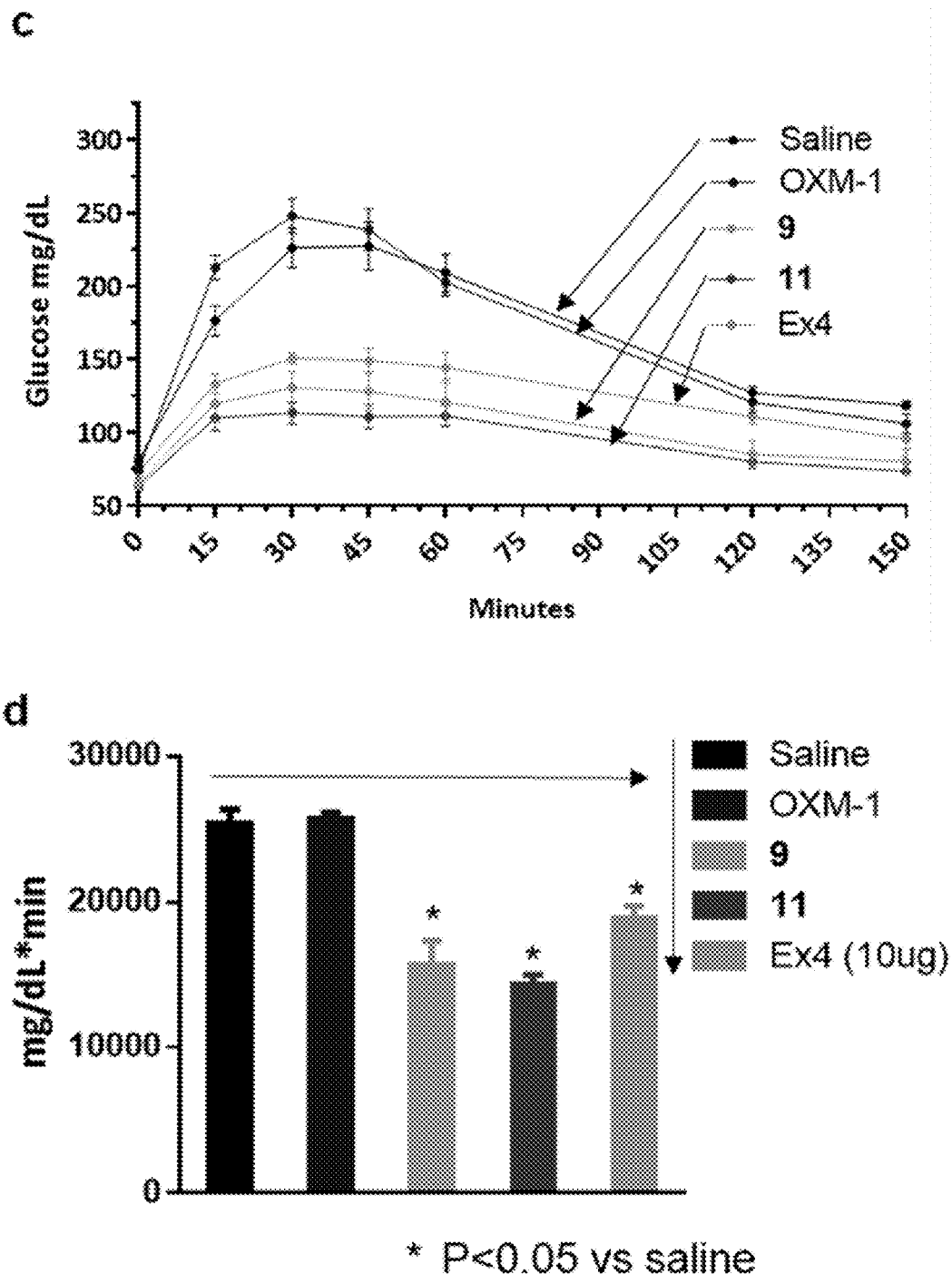

FIG. 2 shows chemical crosslinking extends OXM half-life and efficacy. In vivo stability of the OXM analogs after intravenous (a) and subcutaneous (b) injection of the peptides into mice (n=3). The peptide concentrations in mouse plasma at the various times were determined using the GLP-1R activation assay. Assay was performed in triplicate. Half-lives of the OXM analogs were calculated by fitting the curve to either two-phase exponential decay (i.v) or one-phase exponential decay (s.c) in Prism 6.0. *No clear distinction was detected between the signal and the background. Crosslinked peptides 9 and 11 show greater activity in the oral glucose tolerance test in mice (n=4). Mice were injected with the peptides (10 µg/mice) subcutaneously 4 hours prior to the glucose challenge. (c) The glucose concentrations in mouse blood were monitored for up to 150 minutes. (d) Bar graph showing the total amount of glucose in the mice obtained by measuring the area under curve (AUC).

Figure 3:
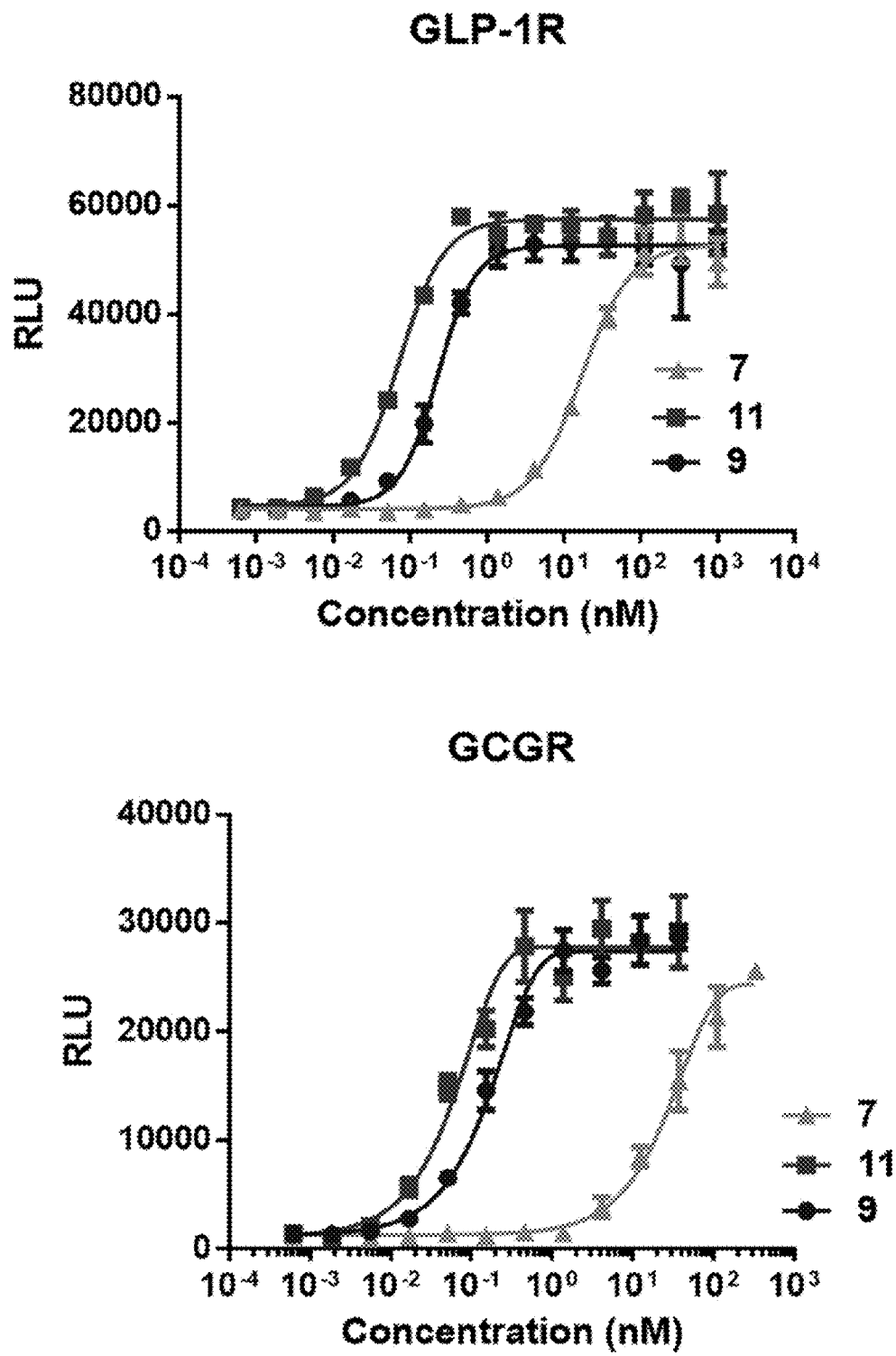

FIG. 3 shows examples of crosslinked OXM analogs that exhibit potent dual-agonist activities. HEK293 cells with GLP1R and GCGR reporters were treated with peptides 7, 9 and 11 at varying concentrations for 16 h, and the luminescent signals were acquired using the Bright-Glo™ Luciferase Assay System. Assays were performed in triplicate and the dose-response curves were fitted to log-agonist vs. response—variable slope in Prism to generate the $EC_{50}$ values.

Figure 4:
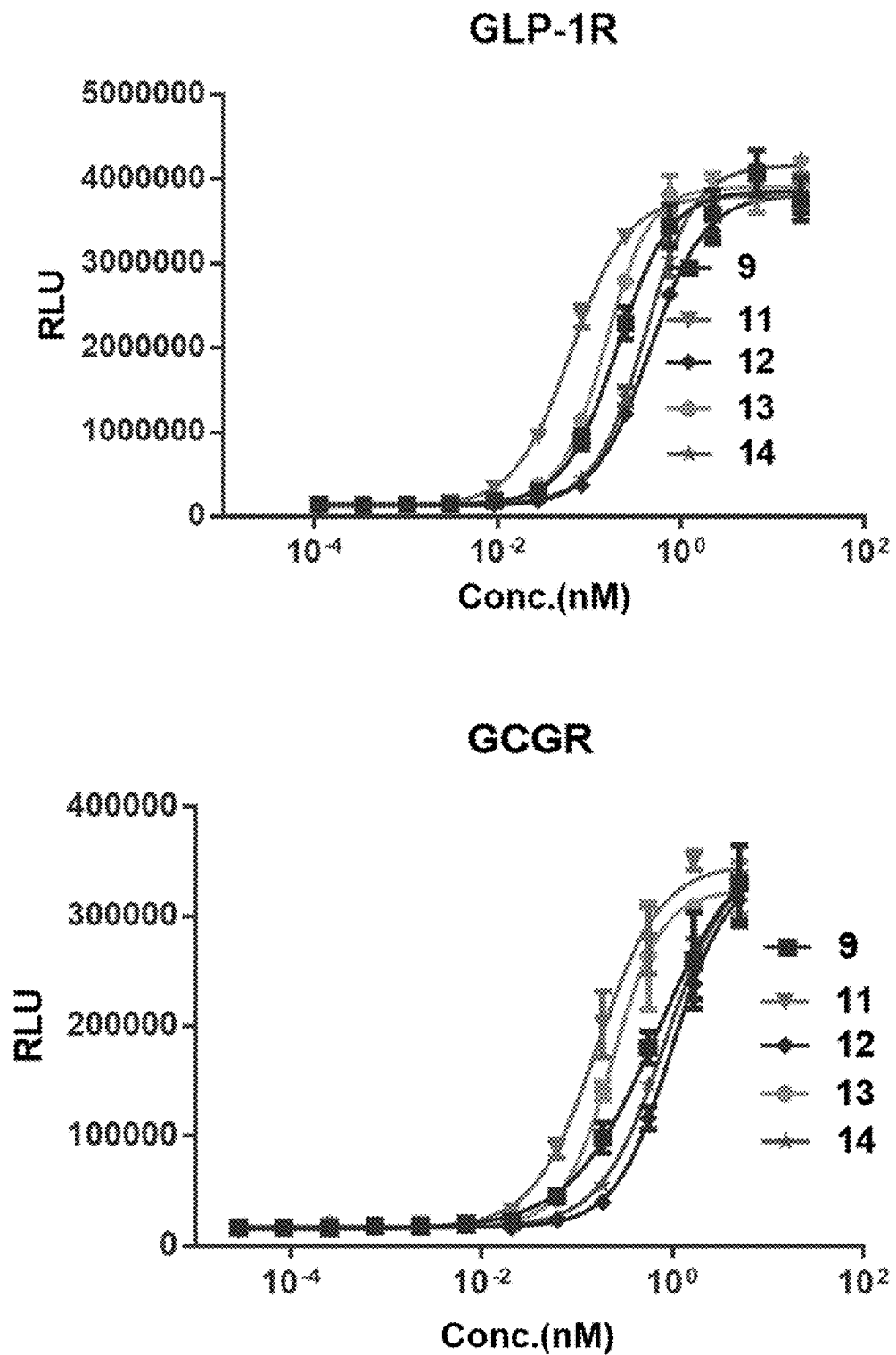

FIG. 4 shows dual-agonist activities of crosslinked analogs of peptide 7 in the luciferase based reporter assay.

Figure 5:
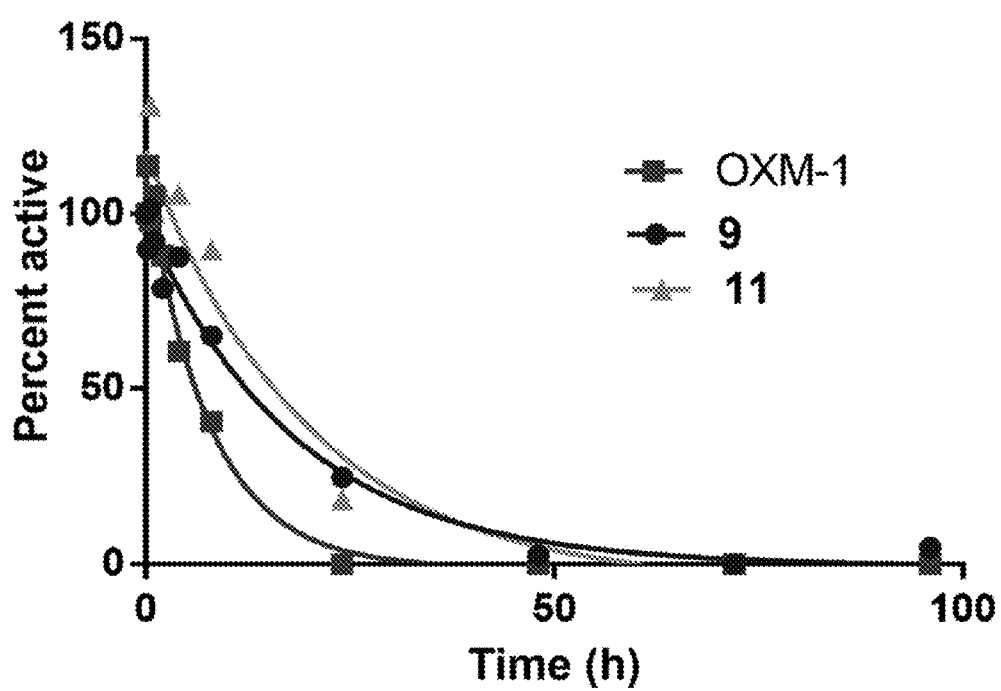

FIG. 5 shows chemical crosslinking extends OXM half-life in vitro. Percent active residual peptides (OXM-1, 9 and 11) as determined by the GLP-1R activation assay. Aliquots were withdrawn at various times from mouse serum incubated with the peptides. Assay was performed in triplicate.

Figure 6:
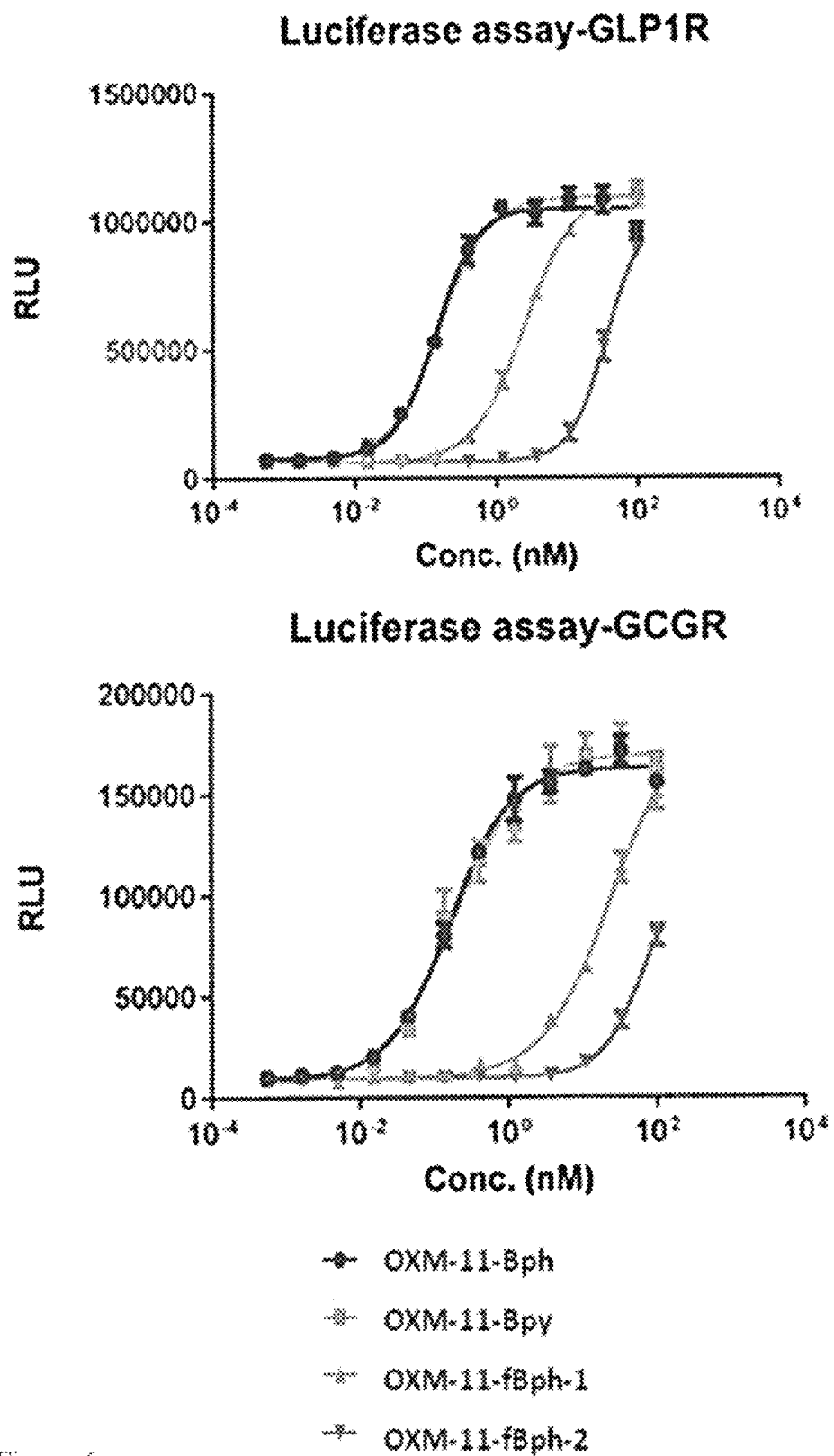

FIG. 6 shows in vitro activity of OXM-11-Bph, OXM-11-Bpy, OX-11-fBph-1, and OXM-11-fBph-2.

DETAILED DESCRIPTION OF THE DISCLOSURE

Although claimed subject matter will be described in terms of certain embodiments and examples, other embodiments and examples, including embodiments and examples that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The present disclosure provides oxyntomodulin (OXM) analog peptides (e.g., crosslinked OXM analog peptides) and fusion proteins thereof and compositions comprising the one or more OXM analog peptides and/or one or more fusion protein thereof. The oxyntomodulin (OXM) analog peptides are also referred to herein as peptides or crosslinked peptides. The present disclosure also provides methods of using the OXM analog peptides and/or fusion proteins thereof. For example, the peptides and/or proteins are used to treat high blood glucose levels and/or induce weight loss in an individual in need of treatment.

In an aspect, the present disclosure provides OXM analog peptides and fusion proteins thereof. The analogs can be crosslinked analogs.

The crosslinked OXM analogs have two cysteine residues. The crosslinking moiety is covalently bonded via a carbon-sulfur bond to the sulfur atoms of the two cysteine residues. The cysteines can be present in OXM peptides or introduced into the OXM analog peptides (replace another amino acid in an OXM peptide). Other amino acids in the peptide can also be replaced with their D isomers. For example, the serine in position number 2 (e.g., the serine in position number 2 of SEQ ID NO. 2) can be D-serine.

The two cysteines are spaced apart such that they can be crosslinked using a suitable crosslinking agent. Thus, the crosslinking in the present peptides is intramolecular, i.e., within the same peptide or protein molecule. In an example, there is no inter-molecular crosslinking. For example, the two cysteines can have 6 amino acids between them. The first cysteine (whose position in the peptide, e.g., of SEQ ID NO:1) indicated by i, can be at any position that will not interfere with the binding of the peptide to its receptor. For example, the first six N-terminus amino acids are considered to be involved in receptor binding. In an example, the cys-[Xaa]$_6$-cys cassette can be placed starting at any amino acid from position 7 onwards, where [Xaa] represents any amino acid. The position of the second cysteine involved in crosslinking is indicated as i+7 (indicating there are 6 amino acids between the two cysteines). Position i can be at any position from and including position 7 through position 30. For example, i could be at position 7, 8, 9, 10, 11, 12, 13, 14, 15, 16, 17, 18, 19, 20, 21, 22, 23, 24, 25, 26, 27, 28, 29, or 30 of SEQ ID NO:1 and the corresponding i+7 could be at position 14, 15, 16, 17, 18, 19, 20, 21, 22, 23, 24, 25, 26, 27, 28, 29, 30, 31, 32, 33, 34, 35, 36, or 37 respectively. The cysteines at positions i and i+7 can independently be L-cysteine or D-cysteine.

The OXM analog peptides can be described as having the following sequence: HSQGTFTSDYSKYLDSRRAQD-FVQWLMNTKRNRNNIA (SEQ ID NO:1), or a variant thereof having at least 65% homology with SEQ ID NO:1, in which at least two of the amino acids are replaced with cysteine (e.g., L-cysteine, D-cysteine or a combination thereof). In various examples, the peptide has at least 70%, at least 75%, at least 80%, at least 85%, at least 90%, or at least 95% homology with SEQ ID NO:1, in which at least two of the amino acids are replaced with cysteine. In various examples, the peptide can have the first six amino acids unchanged and have at least a 65% homology, at least 70%, at least 75%, at least 80%, at least 85%, at least 90%, or at least 95% homology with SEQ ID NO:1 with the remaining sequence represented by amino acids 7 through 37. For example, an OXM analog peptide has a serine at position number two of SEQ ID NO:1.

The C-terminus of a peptide may be truncated. For example, from 1 to 8 C-terminal amino acids of SEQ ID NO:1 may be absent. The truncated sequence of the peptide, if eight C-terminal amino acids (KRNRNNIA (SEQ ID NO:9)) are absent, is HSQGTFTSDYSKYLDSRRAQD-FVQWLMNT (SEQ ID NO:10). Thus, a peptide of the present disclosure can have the sequence of SEQ ID NO:10 or a variant thereof that has at least 65% homology (e.g., at least 70%, at least 75%, at least 80%, at least 85%, at least 90%, or at least 95% homology) to the entire sequence or to a portion of the sequence from amino acid 7 to 29, and which comprises the Cys-[Xaa]$_6$-Cys cassette, with the first Cys being at any position from number 7 to 22 and the i+7 cysteine being at any position from 14 to 29, respectively.

In the Cys-[Xaa]₆-Cys cassette, [Xaa]₆ sequence can be RAQDFV (SEQ ID NO:3), AAKEFI (SEQ ID NO:4), AVRLFI (SEQ ID NO:5), or can be a sequence having at least 80% homology (e.g., at least 85%, at least 90%, or at least 95% homology) with SEQ ID NO:3, SEQ ID NO:4, or SEQ ID NO:5. The peptides of the present disclosure can have the following structure: $[X]_a$-$[X]_b$-C-$[X]_c$-C'-$[X]_d$. $[X]_a$ has a sequence HSQGTFTSDYSKYLD (SEQ ID NO:2) or a sequence having at least 80% homology (e.g., at least 85%, at least 90%, or at least 95% homology) to SEQ ID NO:2. $[X]_b$ is serine or glutamic acid. $[X]_c$ has a sequence RAQDFV (SEQ ID NO:3), AAKEFI (SEQ ID NO:4), AVRLFI (SEQ ID NO:5), or a sequence having at least 80% homology (e.g., at least 85%, at least 90%, or at least 95% homology) with SEQ ID NO:3, SEQ ID NO:4, or SEQ ID NO:5. $[X]_d$ has a sequence WLMNTKRNRNNIA (SEQ ID NO:6) or a sequence having at least 80% homology (e.g., at least 85%, at least 90%, or at least 95% homology) with SEQ ID NO:6. C and C' can independently be L-cysteine or D-cysteine. For example, an OXM analog peptide has a serine at position number two of SEQ ID NO: 2.

The OXM analog peptides of the present disclosure can have the following structure: $[X]_e$-C-$[X]_f$-C'-$[X]_g$. $[X]_e$ has a sequence HSQGTFTSDYSKYLDSRRAQ (SEQ ID NO:7) or a sequence having at least 80% homology to SEQ ID NO:7. $[X]_f$ has a sequence FVQWLM (SEQ ID NO:8) or a sequence having at least 80% homology (e.g., at least 85%, at least 90%, or at least 95% homology) with SEQ ID NO:8. $[X]_g$ is TKRNRNNIA (SEQ ID NO:16). C and C' can independently be L-cysteine or D-cysteine. For example, an OXM analog peptide has a serine at position number two of SEQ ID NO: 7.

The OXM analog peptides of the present disclosure can be present in fusion proteins. A fusion protein can comprise one or more OXM analog peptide of the present disclosure. For example, a fusion protein comprises an OXM analog peptide, a peptide linker, and a protein. The protein can be any suitable protein (e.g., transferrin, human IgG Fc variant, etc.).

The two cysteines at i and i+7 within same OXM peptide analog or fusion protein comprising one or more OXM peptide analogy of the present disclosure can be crosslinked thereby providing desired configurations of the peptides or fusion proteins. Various crosslinking moieties may be used to crosslink the cysteine residues at positions i and i+7. It is considered that crosslinking can stabilize the peptide analogs or proteins and/or increase their efficacy.

As an example, when position i is D-cysteine or L-cysteine, and position i+7 is D-cysteine or L-cysteine, C and C' can be crosslinked using various crosslinking moieties. Examples of suitable crosslinking moieties include, but are not limited to:

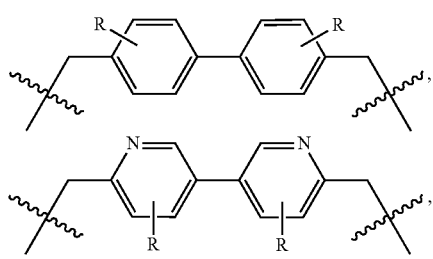

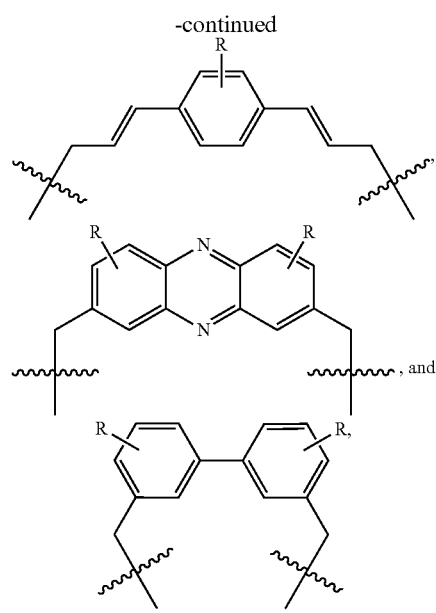

where R at each occurrence is independently a hydrogen, a PEG group, a lipid group (e.g., a lipid-like group), or a PEG moiety further conjugated to a fatty diacid group. An example would be an unsymmetrical crosslinking moiety, wherein R on one aryl ring is an H and R on the other aryl ring is a PEG group, a lipid group, or fatty diacid group. Other examples of suitable crosslinking moieties include, but are not limited to:

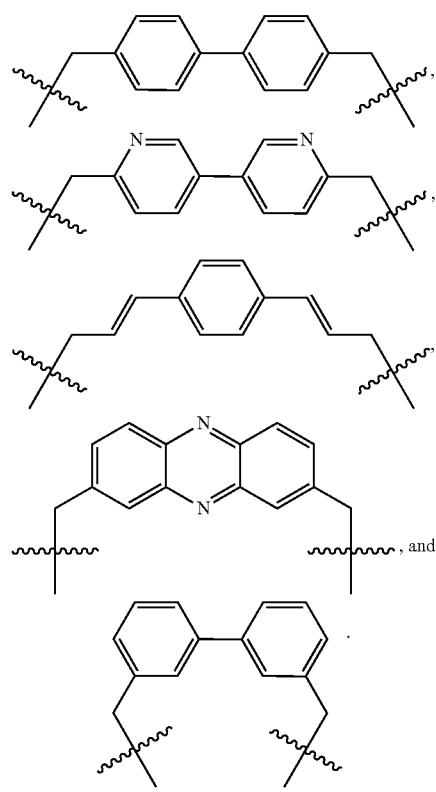

The PEG moiety can have a molecular weight of 20 to 40 kD. In an example, a crosslinking moiety has a PEG moiety having a molecular weight of 40 kD. In another example, a crosslinking moiety has two PEG moieties and each of the PEG moieties have a molecular weight of 20 kD. Examples of fatty diacids that can be separated from the crosslinking moiety by a spacer (e.g., a flexible spacer such as, for example, a PEG moiety spacer) include, but are not limited to

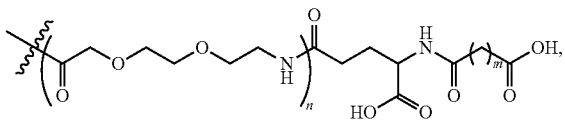

wherein n is 2, and m is 14, 16, 18, or 20.

In various examples, an OXM analog peptide or fusion protein has the following sequence: HSQGTFTSDYSKYL-DECAAKEFICWLMNTKRNRNNIA (SEQ ID NO:11), or a variant thereof with 65% homology to SEQ ID NO:11 (e.g., at least 65%, at least 70%, at least 75%, at least 80%, at least 85%, at least 90%, at least 95%, at least or 99% homology to SEQ ID NO:11), where, optionally, the serine at position number 2 is D-serine, where the cysteine residues are covalently crosslinked, wherein the crosslinking moiety is selected from

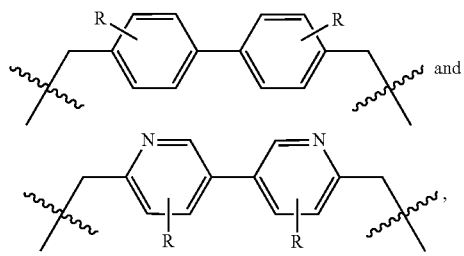

and where R at each occurrence on the crosslinking moiety is independently an H, a polyethylene glycol (PEG) group, a lipid group, or a PEG moiety functionalized with a fatty diacid group. In various examples, R at each occurrence on the crosslinking moiety is an H.

Crosslinking can be performed using suitable reaction conditions known in the art. For example, reactions can be performed by incubating a suitable OXM analog peptide with a slight excess (e.g., 1.01-1.5 equivalent) of a crosslinking agent (e.g., a brominated analog of a crosslinking moiety of the present disclosure) where the crosslinking agent is a in a buffered media (e.g., a mixture of 1:4 to 2:3 acetonitrile/water containing 30 mM $NH_4HCO_3$), with stirring for several hours. The product can be recovered through methods known in the art such as, for example, sublimation (e.g., lyophilization). Further purification can be performed using methods known in the art such as, for example, chromatography (e.g., HPLC). As an example, washing the lyophilized residue with an organic solvent (e.g., diethyl ether), followed by purification of the rinsed material by preparative HPLC. Without intending to be bound by any particular theory, it is considered that intermolecular crosslinking is prevented because intramolecular crosslinking is kinetically favored.

Crosslinked OXM analogs can be PEGylated. Accordingly, in an example, a crosslinked OXM analog has one or more PEG groups conjugated (e.g. covalently bound) to the OXM analog. Suitable PEG polymers are typically commercially available or may be made by techniques well-known to those skilled in the art. The polyethylene glycol (PEG) groups may have a mass (e.g., an average mass) of 20 kD to 40 kD, including all D values therebetween. The PEG groups can be linear or branched. In various examples, PEG groups can be conjugated to the C-terminus, the N-terminus, amino acid sidechains, and any combination thereof.

There are several strategies for conjugating PEG to peptides (see, e.g. Veronese, Biomaterials 22:405-417, 2001, the disclosure of which with respect to conjugation of PEG to peptides is incorporated herein by reference). Those skilled in the art, will therefore be able to utilize well-known techniques for linking PEG to OXM analog peptides described herein.

The lipid group can be a substituent comprising 8 to 40 carbons, including all integer number of carbons and ranges therebetween. The lipid group may further comprise an amino group, at least one free carboxylic acid group, a negatively charged functional group, and any combination thereof. The lipid group can be a straight chain fatty acid which has an amino group. The lipid may contain a spacer. In an example, succinic acid, glutamic acid, and aspartic acid may be used as spacers. When succinic acid is used as a spacer, one of its carboxyl groups can form an amide bond with an amino group in the N-terminal amino acid of the parent peptide while the other carboxyl group can form an amide bond with an amino group contained in the bulk lipophilic group. When glutamic acid or aspartic acid is used as a spacer, one of the carboxyl groups can form an amide bond with an amino group in the N-terminal amino acid of the parent peptide while the bulk lipophilic substituent can be the alkyl group of a straight chain fatty acid. In another example, an additional free carboxy group on the fatty acid may form an amide bond with lysine or an ester bond with serine.

There are various strategies for coupling lipids and lipid-like moieties to peptides (see, e.g. U.S. Pat. No. 7,576,059, the disclosure of which with respect to coupling lipids and lipid-like moieties to peptides is incorporated herein by reference). Those skilled in the art, will therefore be able to utilize well-known techniques for linking lipids to the OXM analog peptides described herein.

The OXM analog peptides of the present disclosure have increased circulatory half-life and/or potency toward GLP-1R and GCGR. OXM exhibits high sequence homology with glucagon-like peptide-1 (GLP-1) and glucagon (GCG), an incretin peptide. The N-termini of OXM and the peptides of the present disclosure activate the GLP-1 receptor (GLP-1R) and the GCG receptor (GCGR). Activation of GLP-1 and/or GCG increases the insulin secretion of the pancreas. An increase in insulin release will in turn decrease blood glucose levels.

In an aspect, the present disclosure provides compositions comprising one or more OXM analog peptides and/or fusion proteins of the present disclosure. The OXM analog peptides and/or fusion proteins can be crosslinked OXM analog peptides and/or crosslinked fusion proteins.

OXM analog peptides can be provided in pharmaceutical compositions for administration by combining them with any suitable pharmaceutically acceptable carriers, excipients, stabilizers, or a combination thereof. Examples of pharmaceutically acceptable carriers, excipients, and stabilizers can be found in *Remington: The Science and Practice of Pharmacy* (2005) 21st Edition, Philadelphia, Pa. Lippincott Williams & Wilkins. For example, suitable carriers include excipients and stabilizers which are nontoxic to recipients at the dosages and concentrations employed, and include buffers such as, for example, acetate, Tris, phosphate, citrate, and other organic acids; antioxidants including ascorbic acid and methionine; preservatives such as, for example, octadecyldimethylbenzyl ammonium chloride; hexamethonium chloride; benzalkonium chloride, benzethonium chloride; phenol, butyl or benzyl alcohol; alkyl parabens such as, for example, methyl or propyl paraben; catechol; resorcinol; cyclohexanol; 3-pentanol; and m-cresol; amino acids such as, for example, glycine, glutamine, asparagine, histidine, arginine, or lysine; monosaccharides, disaccharides, and other carbohydrates including glucose, mannose, or dextrins; chelating agents such as, for example, EDTA; tonicifiers such as, for example, trehalose and sodium chloride; sugars such as, for example, sucrose, mannitol, trehalose or sorbitol; surfactant such as, for example, polysorbate; salt-forming counter-ions such as, for example, sodium; and/or non-ionic surfactants such as, for example, Tween or polyethylene glycol (PEG). The pharmaceutical compositions may comprise other therapeutic agents. The present compositions can be provided as single doses or in multiple doses covering the entire or partial treatment regimen. The compositions can be provided in liquid, solid, semi-solid, gel, aerosolized, vaporized, or any other form from which it can be delivered to an individual.

In an aspect, the present disclosure provides uses of OXM analogs of the present disclosure. For example, OXM analogs can be used for treatment for obesity, diabetes (including type 2 diabetes), weight gain, or disorders associates with high blood glucose levels.

The compositions can be administered to an individual in need of treatment for obesity, diabetes (including type 2 diabetes), weight gain, or disorders associates with high blood glucose levels. Clinicians will be able to assess individuals who are in need of being treated for these conditions or individuals themselves may be able to assess a need for intake of these compositions. The present compositions can be used in combination with other diagnostic approaches and/or therapeutic approaches for the conditions. The additional therapeutic approaches can be carried out sequentially or simultaneously with the treatment involving the present compositions.

As used herein, "treatment" of diabetes is not limited to treatment, but encompasses alleviation of the symptoms of diabetes and management of blood glucose levels.

Administration of formulations comprising OXM peptides as described herein can be carried out using any suitable route of administration known in the art. For example, the compositions comprising OXM peptides may be administered via intravenous, intramuscular, intraperitoneal, intracerobrospinal, subcutaneous, intra-articular, intrasynovial, oral, topical, or inhalation routes. The compositions may be administered parenterally or enterically. The compositions may be introduced as a single administration or as multiple administrations or may be introduced in a continuous manner over a period of time. For example, the administration(s) can be a pre-specified number of administrations or daily, weekly or monthly administrations, which may be continuous or intermittent, as may be clinically needed and/or therapeutically indicated.

In the following Statements, various examples of OXM analogs of the present disclosure and uses thereof are described:

Statement 1.

A crosslinked peptide (a crosslinked OXM analog peptide) having the following sequence: HSQGTFTSDYSKY-LDSRRAQDFVQWLMNTKRNRNNIA (SEQ ID NO:1), or a variant thereof having at least 65% homology with SEQ ID NO:1, wherein a first amino acid at position i and a second amino acid at position i+7 are replaced independently by L-cysteine or D-cysteine, wherein i can be at any position from and including number 7 to number 30, wherein the peptide is crosslinked with a crosslinking moiety between the cysteines at i and i+7 and wherein the crosslinking moiety is selected from the group consisting of:

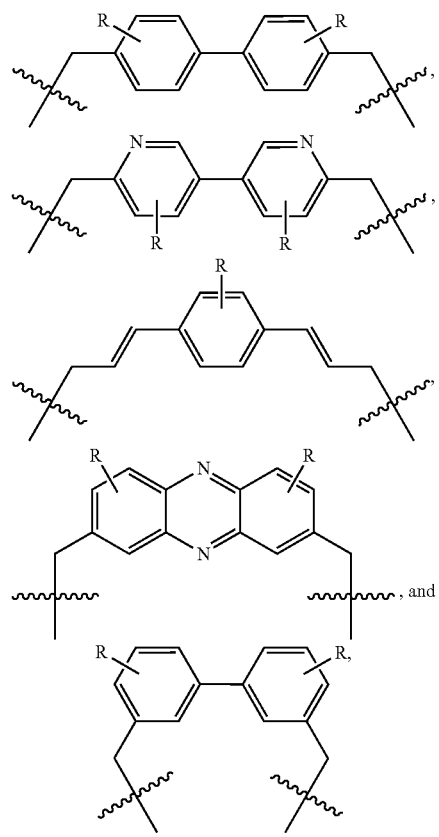

and wherein R at each occurrence is independently an H, a polyethylene glycol (PEG) group, a lipid group, or a PEG moiety (e.g., spacer moiety) functionalized with a fatty diacid group.

Statement 2.

A crosslinked peptide according to Statement 1, where i can be at position number 17 or number 21.

Statement 3.

A crosslinked peptide according to any one of Statements 1 or 2, where the serine at position 2 is D-serine.

Statement 4.

A crosslinked peptide according to any one of the preceding Statements, wherein the peptide is conjugated with at least one polyethylene glycol group and/or at least one lipid group (e.g., a lipid group with a PEG linker) and/or at least one fatty diacid group (e.g., a fatty acid group with a PEG linker).

Statement 5.

A crosslinked peptide according to any one of the preceding Statements, where the amino acids at positions i+2 to i+6 have a sequence selected from the group consisting of: RAQDFV (SEQ ID NO:3), AAKEFI (SEQ ID NO:4), AVRLFI (SEQ ID NO:5), and a sequence having at least 80% homology with SEQ ID NO:3, SEQ ID NO:4, or SEQ ID NO:5.

Statement 6.

A crosslinked peptide according to any one of the preceding Statements, where the peptide has the following structure: HsQGTFTSDYSKYLDECAAKEFICWLMNT-KRNRNNIA (SEQ ID NO:11).

Statement 7.

A crosslinked peptide according to any one of the preceding Statements, wherein the crosslinking moiety is selected from the group consisting of:

[chemical structures: biphenyl and bipyridyl crosslinkers with R substituents] and Statement 8.

A crosslinked peptide according to any one of the preceding Statements, wherein R at each occurrence on the crosslinking moiety is an H.

Statement 9.

A fusion protein comprising one or more crosslinked peptide of any one of the preceding Statements, a peptide spacer, and a protein.

Statement 10.

A composition comprising a peptide of any one of Statements 1 to 8 or a fusion protein of Statement 9 and a pharmaceutically acceptable carrier.

Statement 11.

A method of lowering blood glucose level in an individual in need of treatment comprising: administering a crosslinked peptide of any one of Statements 1 to 8, a fusion protein of Statement 9, a composition of Statement 10, or a combination thereof to the individual, where the administration results in a lowered blood glucose level in the individual.

Statement 12.

A method of inducing weight loss of an individual in need of treatment comprising: administering a crosslinked peptide of any one of Statements 1 to 8, a fusion protein of Statement 9, a composition of Statement 10, or a combination thereof to the individual, where the administration results in a lowered blood glucose level.

The steps of the methods described in the various embodiments and examples disclosed herein are sufficient to carry out the methods of the present invention. Thus, in an embodiment, a method consists essentially of a combination of the steps of the methods disclosed herein. In another embodiment, a method consists of such steps.

The following examples are presented to illustrate the present disclosure. They are not intended to limiting in any matter.

Example 1

This example provides a description of the preparation, characterization, and use of OXM analogs of the present disclosure.

Figure 1:
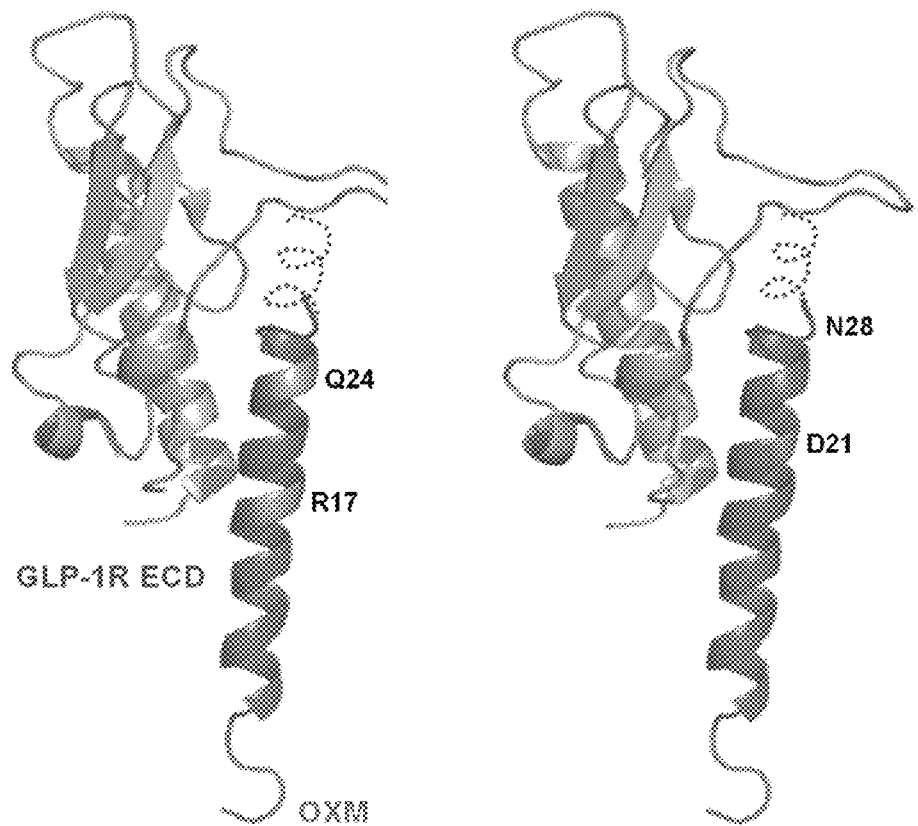
FIG. 1 shows (a) sequences of oxyntomodulin (SEQ ID NO:1), glucagon (SEQ ID NO:10), GLP-1 (SEQ ID NO:17) and exendin-4 (SEQ ID NO:18). The conserved N-terminal residues important for receptor activation are underlined. The sites for cysteine substitution and subsequent crosslinking on oxyntomodulin are identified. (b) Structural model of oxyntomodulin bound to the extracellular domain of GLP-1R (PDB code 3C59), with the crosslinking sites indicated.

OXM contains a C-terminal extension of glucagon and also exhibits high sequence homology with the incretin peptide, GLP-1 (FIG. 1a). In order to facilitate biaryl crosslinking without disrupting receptor binding, residues that are solvent exposed and oriented on the same side of the helix, i.e., residues at i and i+7 positions, were replaced with D- and L-cysteine, respectively. Since the N-termini of these peptides are highly conserved and play a crucial role in activation of GLP-1 receptor (GLP-1R), we focused on Cys substitutions at the C-terminus of OXM. To predict which residues are solvent exposed, glucagon was superimposed with GLP-1 in the binding pocket of GLP-1R (FIG. 1b). Because of its high sequence identity with glucagon, we predicted that the N-terminus of OXM, OXM (1-29), will adopt the same bound conformation as the full-length glucagon. We also hypothesized that the octapeptide extension of OXM, OXM (30-37), will exhibit a type II β-helical turn. Based on this homology model, we generated two OXM mutants with pairs of solvent-exposed D- and L-cysteine residues that are separated by 6 residues (R17 and Q24; D21 and N28), and which most likely not involved in direct binding to the extracellular domain of GLP-1R and GCGR.

We used the DPP-IV resistant OXM, OXM-1 (OXM with D-serine at $2^{nd}$ position), as a template for cysteine substitution and subsequent sidechain crosslinking. To assess how chemical modification affects receptor activation, we developed a cAMP response element (CRE) driven luciferase reporter for HEK293 cells overexpressing GLP-1R and GCGR receptors. The $EC_{50}$ values of OXM-1 for GLP-1R and GCGR were 10 nM and 3 nM, respectively (Table 1). We then tested the activity of the linear di-cysteine substituted peptides 1 (R17 and Q24 are substituted with D and L-cysteine, respectively) and 2 (D21 and N28 are substituted with D and L-cysteine, respectively). Both 1 and 2 showed reduced potency for GLP-1R activation, but peptide 1 activated GCGR more potently than peptide 2. Hence, we proceeded to crosslink 1 with 4,4'-bis(bromomethyl)biphenyl (Bph), to generate peptide 3. Although crosslinking increased the activities toward both GCGR (16-fold) and GLP-1R (2-fold) compared to its linear counterpart, peptide 3 still exhibited substantially reduced activity compared to OXM-1. Since a D-amino acid in the middle of a helical peptide can cause helix distortion, we substituted R17 with L-cysteine and generated peptide 4 (both R17 and Q24 are substituted with L-cysteine). Although we anticipated that L-Cys17 might have a less favorable geometry for crosslink formation, peptide 4 showed roughly 2-fold increase in GLP-1R and GCGR activities compared to its D,L counterpart, peptide 1.

To further increase receptor activity, we next generated a chimera OXM by incorporating key binding residues from the GLP-1 agonists GLP-1 and exendin-4 (Ex-4). We synthesized peptide 5 by replacing Ser16 with Glu in peptide 4, and found modest enhancement in the GLP-1R and GCGR activities. Because incorporation of residues from exendin-4 or GLP-1 in the middle of the glucagon sequence significantly increases GLP-1R activity, we substituted GLP-1 residues (AAKEFI; SEQ ID NO:4) and exendin-4 residues (AVRLFI; SEQ ID NO:5) in the middle of peptide 5 (RAQDFV; SEQ ID NO:3) to afford peptides 7 and 8, respectively (Table 1). We found that peptides 7 and 8 showed >80-fold higher potency in GLP-1R activation, compared to peptide 5, although peptide 8 was less potent in GCGR activation (Table 1). Crosslinking of 7 led to 80- and 40-fold increases in activity for GLP-1R and GCGR, respectively, giving rise to a balanced subnanomolar dual agonist peptide 9 for potent activation of both receptors ($EC_{50}$=0.2 nM for GLP-1R, and 0.7 nM for GCGR; Table 1).

TABLE 1

Sequences of the modified oxyntomodulin analogs and their agonist activities in the activation of GLP-1R and GCGR using the cell-based luciferase reporter assay[a]

| Name | SEQ ID NO: | Sequence | Agonist activity (nM) GLP-1R | GCGR |
|---|---|---|---|---|
| OXM-1 | 1[1] | HsQGTFTSDYSKYLDSRRAQDFVQWLMNTKRNRNNIA | 10 | 3 |
| 1 | 12[2] | HsQGTFTSDYSKYLDScRAQDFVCWLMNTKRNRNNIA | 1000 | 50 |
| 2 | 13[3] | HsQGTFTSDYSKYLDSRRAQcFVQWLMCTKRNRNNIA | >2000 | >1000 |
| 3 | 12[4] | HsQGTFTSDYSKYLDSc'RAQDFVC'WLMNTKRNRNNIA[b] | ~500 | 3 |
| 4 | 12[5] | HsQGTFTSDYSKYLDSCRAQDFVCWLMNTKRNRNNIA | ~500 | 30 |
| 5 | 14[6] | HsQGTFTSDYSKYLDECRAQDFVCWLMNTKRNRNNIA | ~400 | 20 |
| 6 | 14[7] | HsQGTFTSDYSKYLDEC'RAQDFVC'WLMNTKRNRNNIA | ~100 | 0.8 |
| 7 | 11[8] | HsQGTFTSDYSKYLDECAAKEFICWLMNTKRNRNNIA | 17 | 30 |
| 8 | 15[9] | HsQGTFTSDYSKYLDECAVRLFICWLMNTKRNRNNIA | 1 | 1000 |
| 9 | 11[10] | HsQGTFTSDYSKYLDEC'AAKEFIC'WLMNTKRNRNNIA | 0.2 | 0.7 |
| 10 | 15[11] | HsQGTFTSDYSKYLDEC'AVRLFIC'WLMNTKRNRNNIA | 56 | ~200 |

[a]All peptides contain the unmodified N-termini and the amidated C-termini.
[b]c' and C' denote the Bph-crosslinked D-cysteine and L-cysteine, respectively.
[1]SEQ ID NO: 1, where the serine at position 2 has been replaced with D-serine.
[2]SEQ ID NO: 12, where the serine at position 2 has been replaced with D-serine, and the cysteine at position 17 is D-cysteine.
[3]SEQ ID NO: 13, where the serine at position 2 has been replaced with D-serine, and the cysteine at position 21 has been replaced with D-cysteine.
[4]SEQ ID NO: 14, where the serine at position 2 has been replaced with D-serine, the cysteine at position 17 is D-cysteine, and the two cysteines are crosslinked with the crosslinking moiety Bph.
[5]SEQ ID NO: 12, where the serine at position 2 has been replaced with D-serine.
[6]SEQ ID NO: 14, where the serine at position 2 has been replaced with D-serine.
[7]SEQ ID NO: 14, where the serine at position 2 has been replaced with D-serine and the two cysteines are crosslinked with the crosslinking moiety Bph.
[8]SEQ ID NO: 11, where the serine at position number 2 has been replaced with D-serine.
[9]SEQ ID NO: 15, where the serine at position 2 has been replaced with D-serine.
[10]SEQ ID NO: 11, where the serine at position number 2 has been replaced with D-serine and the two cysteines are crosslinked with the crosslinking moiety Bph.
[11]SEQ ID NO: 15, where the serine at position number 2 has been replaced with D-serine and the two cysteines are crosslinked with the crosslinking moiety Bph.

Having identified the optimal di-cysteine-containing OXM sequence, we next modified peptide 7 using a panel of cysteine-reactive crosslinkers: Bpy (CL-2), Alk (CL-3), Phen (CL-4) and mBph (CL-5) (see Table 2 for structures). Crosslinked peptide 11 showed even more potent agonist activities in dual activation of GLP-1R and GCGR with $EC_{50}$ values of 0.07 nM and 0.18 nM, respectively (FIG. 4).

TABLE 2

Structures and agonist activities of the various crosslinked analogs of peptide 7.

| OXM Sequences | SEQ ID NO: | Crosslinker structure | Agonist activity (nM)[a] GLP-1R | GCGR |
|---|---|---|---|---|
| 9 | 11[1] | 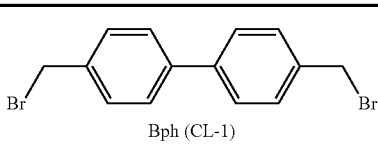 Bph (CL-1) | 0.20 ± 0.05 | 0.74 ± 0.30 |

TABLE 2-continued

Structures and agonist activities of the various crosslinked analogs of peptide 7.

| OXM Sequences | SEQ ID NO: | Crosslinker structure | Agonist activity (nM)[a] | |
|---|---|---|---|---|
| | | | GLP-1R | GCGR |
| 11 | 11[2] | Bpy (CL-2) | 0.07 ± 0.01 | 0.18 ± 0.02 |
| 12 | 11[3] | Alk (CL-3) | 0.45 ± 0.03 | 1.00 ± 0.12 |
| 13 | 11[4] | Phen (CL-4) | 0.15 ± 0.02 | 0.24 ± 0.12 |
| 14 | 11[5] | mBph (CL-5) | 0.40 ± 0.02 | 0.84 ± 0.15 |

[a]Luciferase reporter assay was performed three times to derive mean $IC_{50}$ values and standard deviations.
[1]SEQ ID NO:11, where serine at position 2 is D-serine and the cysteines are crosslinked with Bph.
[2]SEQ ID NO:11, where serine at position 2 is D-serine and the cysteines are crosslinked with Bpy.
[3]SEQ ID NO:11, where serine at position 2 is D-serine and the cysteines are crosslinked with Alk.
[4]SEQ ID NO:11, where serine at position 2 is D-serine and the cysteines are crosslinked with Phen.
[5]SEQ ID NO:11, where serine at position 2 is D-serine and the cysteines are crosslinked with mBph.

To gain insight into structural basis for the increased activity after crosslinking, we compared the far-UV circular dichroism spectra of 9 and 11 to that of OXM-1. All three spectra showed local minima at 208 and 222 nm, indicating the presence of an α-helix. The percent helicity, ca. in the range of 20-23%, was found to be similar based on the $[\theta]_{222}$ values, suggesting that the differences in agonist activity cannot be explained by percent helicity. However, we observed a significant difference in the ratio of $[\theta]_{222}/[\theta]_{208}$, a measure of the relative amounts of 310- and α-helix in the conformational ensemble, as 9 and 11 showed ratios close to 1.0 indicating ideal α-helices whereas OXM-1 showed a ratio of 0.68. Assuming the $3_{10}$-helix represents an unproductive conformation, the lack of $3_{10}$-helix from the conformational ensemble may be beneficial to the receptor binding, although other factors other than secondary structures may also affect the binding. For example, despite having similar CD spectra, peptide 11 has 3-4 fold greater efficacy in receptor activation than peptide 9 (Table 1). This difference can be explained by the presence of the pyridyl nitrogen in the Bpy structure, which may form a hydrogen bond with Glu-128 of the extracellular domain of GLP-1R.

To determine the half-lives of the OXM peptides, we performed pharmacokinetic (PK) studies in mice by injecting the peptides through either subcutaneous (s.c) or intravenous (i.v) routes. The peptide concentrations in the plasma at different time points were measured indirectly using the cell-based luciferase reporter assay (the detection limit for peptide concentration in mouse serum is ~10 nM). The concentration of OXM-1 was negligible after 1 h when injected either i.v or s.c., as evidenced by no receptor activation (<10 nM). The elimination half-lives of the intravenously injected peptides were found to be 0.1 h, 1.2 h and 1.4 h for OXM-1, 9 and 11, respectively (FIG. 2a). When administered subcutaneously, the half-lives of OXM-1, 9 and 11 were found to be 0.6 h, 1.9 h and 1.9 h, respectively (FIG. 2b). When the cell-based reporter assay was employed to determine the half-life of the peptide in vitro after incubation with freshly isolated mouse serum, a similar trend was observed ($t_{1/2}$=5.4 h for OXM-1 vs. 13 h for 9 and 11) (FIG. 5). The greater half-lives observed for the crosslinked OXMs in vivo may result from enhanced serum albumin binding by the crosslinked peptides as we have observed previously. The in vivo half-lives can be further improved by modifying the aryl crosslinker with a short PEG-fatty acid moiety.

Since OXM is known to reduce blood glucose levels in diabetic patients, we evaluated the efficacy of the crosslinked OXM analogs in an oral glucose tolerance test (OGTT). As a positive control, Ex-4 significantly decreased the blood glucose level during the entire monitoring period (FIG. 2c) and the area under curve (AUC) by 30% (FIG. 2d), whereas OXM-1 did not exhibit any improvement over the vehicle. Peptides 9 and 11 significantly decreased blood glucose levels to 40 and 45%, respectively, which are greater than that of Ex-4 (FIG. 2c, 2d). The increased in vivo efficacies of the crosslinked peptides observed here likely result from both higher dual-agonist activities (Tables 1 and 2) and the extended in vivo half-lives (FIG. 2a, 2b).

In summary, we have designed a class of chemically crosslinked OXM analogs that show balanced, sub-nanomolar activities in activating the GLP-1 and glucagon receptors. While the crosslinking only marginally increased peptide helicity, substantial improvements in dual-agonist activity as well as in vivo stability were obtained, which makes this approach amenable to chemical modification strategies such as PEGylation which can result in reduced OXM potency. The combined high potency and enhanced in vivo stability resulted in greater efficacy in the oral glucose tolerance test, even at very low dosages (10 μg/mice), highlighting the potential of this technology to obviate the need for high-dose administration of the peptide drugs. The present peptides can be useful in crosslink diet induced obesity paradigms as well as for modification of the crosslinkers with lipid moieties to further enhance in vivo half-life.

TABLE 3

ESI-MS characterization of the crosslinked OXM analogs.

| Peptide | SEQ ID NO | Sequence | Mass calculated (Da) | Mass found (Da) |
|---|---|---|---|---|
| 3 | 12[1] | HsQGTFTSDYSKYLDSc[1]RAQDFVC[1]WLMNTKRNRNNIA | 4548.99 | 4549.06 |
| 6 | 14[2] | HsQGTFTSDYSKYLDEC[1]RAQDFVC[1]WLMNTKRNRNNIA | 4591.02 | 4591.11 |
| 9 | 11[3] | HsQGTFTSDYSKYLDEC[1]AAKEFIC[1]WLMNTKRNRNNIA | 4533.01 | 4533.13 |
| 10 | 15[4] | HsQGTFTSDYSKYLDEC[1]AVRLFIC[1]WLMNTKRNRNNIA | 4574.19 | 4574.25 |
| 11 | 11[5] | HsQGTFTSDYSKYLDEC[2]AAKEFIC[2]WLMNTKRNRNNIA[c] | 4535.01 | 4535.10 |
| 12 | 11[6] | HsQGTFTSDYSKYLDEC[3]AAKEFIC[3]WLMNTKRNRNNIA[c] | 4509.12 | 4509.18 |
| 13 | 11[7] | HsQGTFTSDYSKYLDEC[4]AAKEFIC[4]WLMNTKRNRNNIA[c] | 4560.00 | 4560.12 |
| 14 | 11[8] | HsQGTFTSDYSKYLDEC[5]AAKEFIC[5]WLMNTKRNRNNIA[c] | 4533.01 | 4533.17 |

$c^{1-5}$ denotes cysteine alkylated with crosslinkers (CL-1 to CL-5).
[1] SEQ ID NO: 14 where the serine at position 2 has been replaced with D-serine, the cysteine at position 17 is D-cysteine, and the two cysteines are crosslinked with the crosslinking moiety Bph.
[2] SEQ ID NO: 14, where the serine at position 2 has been replaced with D-serine and the two cysteines are crosslinked with the crosslinking moiety Bph.
[3] SEQ ID NO: 11, where the serine at position number 2 has been replaced with D-serine and the two cysteines are crosslinked with the crosslinking moiety Bph.
[4] SEQ ID NO: 15, where the serine at position number 2 has been replaced with D-serine and the two cysteines are crosslinked with the crosslinking moiety Bph.
[5] SEQ ID NO: 11, where serine at position 2 is D-serine and the cysteines are crosslinked with Bpy.
[6] SEQ ID NO: 11, where serine at position 2 is D-serine and the cysteines are crosslinked with Alk.
[7] SEQ ID NO: 11, where serine at position 2 is D-serine and the cysteines are crosslinked with Phen.
[8] SEQ ID NO: 11, where serine at position 2 is D-serine and the cysteines are crosslinked with mBph.

Materials and General Procedures.

All peptides were purchased from Cellmano Biotech Co., Ltd., Hefei, China and InnoPep, San Diego, Calif. 4,4'-Bis-bromomethyl-biphenyl (Bph) and 3,3'-Bis-bromomethyl-biphenyl (mBph) were purchased from TCI America and used directly in crosslinking reaction. 4,4'-Bis-bromomethyl-bipyridyl (Bpy), p-phenylene-3,3'-bis-allylbromide (Alk), bis-bromomethyl-phenazine (Phen), were synthesized according to published procedure. Crosslinked peptides were purified using a Gilson or Shimadzu semi-preparative reverse-phase HPLC system equipped with a Phenomenex C18 column with a flow rate of 5 mL/min and a gradient of 10-90% ACN/$H_2O$ while monitoring at 220 nm and 254 nm. Analytical HPLC was performed using Phenomenex Luna C18 or Kinetex C18 column (250×4.6 mm) with the flow rate set at 1.0 mL/min and UV detection set at 220 and 254 nm. Electrospray LC-MS analysis was performed using a Finnigan LCQ Advantage IonTrap mass spectrometry coupled with a Surveyor HPLC system or using an Agilent 6520 accurate-mass quadrupole-time-of-light (Q-TOF) instrument equipped with reverse phase liquid chromatography and an electrospray ionization (ESI) source.

Crosslinking Reactions:

Crosslinking reactions were carried out by incubating the purified cysteine-containing peptides with 1.5 equivalent of crosslinkers (Bph/Bpy/Alk/Phen/mBph) in a mixed acetonitrile/water (1:4 to 2:3 depending on solubility) containing 30 mM $NH_4HCO_3$ buffer, pH 8.5, to obtain a final peptide concentration of 1 mM. The mixture was stirred at room temperature for 1.5-2 h. Afterwards the reaction mixture was lyophilized, and the lyophilized powder was washed with diethyl ether to remove excess crosslinker. The residue was dissolved in ACN/$H_2O$, 0.05% TFA and purified by preparative HPLC.

Generation of CREB Responsive Luciferase Stable Cell Lines:

A CREB responsive luciferase stable HEK 293 cell line overexpressing either human glucagon receptor (GCGR) or glucagon-like peptide 1 receptor (GLP-1R) was generated as follows: HEK293 cells were infected with Lentivirus encoding firefly luciferase gene under control of the CRE promoter (Qiagen, Netherlands) and then were selected using 1 μg/mL puromycin (Life technologies, Carlsbad) for 1 week. The surviving cells (referred to as CRE-HEK293) were expanded and then transfected with a G418 selective mammalian expression plasmid encoding human GCGR or GLP-1R, followed by geneticin selection (Life technologies, Carlsbad, Calif.). Single-colony stable cell lines expressing both CRE-luciferase and GCGR/GLP-1R were then established for in vitro activity assays.

In Vitro Receptor Activation Reporter Assays:

HEK293-GCGR-CRE and HEK293-GLP-1R-CRE cells were seeded in a white 384-well plate at a density of 5,000 cells per well and cultured for 24 hours in DMEM with 10% FBS at 37° C. with 5% $CO_2$. Cells were treated with different peptides in a dose dependent manner. After 24 hours, 10 μL of Bright-Glo reagent (Promega, Madison, Wis.) was added to each well and luminescence was determined using an Envision multilabel plate reader (PerkinElmer, Waltham, Mass.). The $EC_{50}$ of each peptide was calculated using GraphPad Prism 6 software (GraphPad, San Diego, Calif.).

Circular Dichroism (CD) Measurement:

CD spectra were recorded with an AVIV model 202SF CD spectrometer at 25° C. in a 0.2-cm pathlength cuvette. The spectra were recorded in the wavelength range 185-250 nm and averaged over 2 scans with a resolution of 0.5 nm, a bandwidth of 1.0 nm and a response time of 4 s. The sensitivity and scan rate of the spectrophotometer were set to 100 mdeg and 50 nm/min, respectively. All peptides were dissolved in 0.1×PBS to reach final concentrations of 0.2 mg/mL. The mean residue ellipticity was plotted vs wavelength, and the percent helicity of each peptide was calculated based on $[\theta]_{222}/[\theta]_{max}$. $[\theta]_{max}$ was calculated according to the formula: $[\theta]_{max}=-39500\,(1-3/n)$ where n is the number of amide bonds.

Molecular Modeling Studies:

The coordinates for GLP-1 complexed with GLP-1R was obtained from the PDB Code: 3C589. Glucagon (PDB code: 1GCN) was aligned with GLP-1 and the two L-Cys substitutions were introduced to replace Arg-17 and Gln-24 of Glucagon and the resulting peptide was energy-minimized using the Amber 99 force field in Hyperchem 8 and Bpy crosslinker was constructed and connected to sulfhydryl groups of the cysteines. Then, the crosslinked peptide-GLP-1 complex was subjected to energy minimization in Hyperchem 8 before calculating the distance between the pyridyl nitrogen and the Glu-128 of GLP-1R ECD.

In Vivo Pharmacokinetic (PK) Studies:

All animal care and experimental procedures were approved by the Institutional Animal Care and Use Committee (IACUC) of California Institute for Biomedical Research and strictly followed the NIH guidelines for humane treatment of animals. Female CD-1 mice obtained from Charles River Limited were used after overnight food deprivation for in vivo PK studies. Peptides were dissolved in pH adjusted phosphate buffered saline (PBS, pH=7.4). 100 μL of each peptide (0.3 mg/kg) was administered to each mouse by either i.v. or s.c routes. Food was provided to mice immediately after bleeding at 30 minutes. Blood was extracted into heparinized tubes and centrifuged at 3,000×g for 15 min. The resulting supernatant plasma was then stored at −80° C. for peptide concentration determination. Peptide concentration in the plasma was determined by in vitro GLP1R activation reporter assay.

PK Determination:

HEK 293 cells overexpressing GLP1R and CRE-Luc reporter were treated with plasma samples at different time points (5 point dose response, starting from 1:20 dilution of each plasma sample), incubated for 16 hours in DMEM with 10% FBS at 37° C. with 5% $CO_2$, and the firefly luciferase activity was measured. At the same time, injected peptides were used to obtain standard curves and parameters for Bottom, Top, $EC_{50}$, Hill Slope. Random luciferase unit (RLU) for each plasma sample was used to calculate the peptide concentrations in plasma (nmol/L), using parameters derived from the standard curve (RLU=Bottom+(Top−Bottom)/(1+10^((Log $EC_{50}$−Conc.)*Hill Slope)). Peptide concentrations in plasma were obtained and plotted against time points to obtain in vivo half-life of each peptide, using WinNonLin Phoenix software (Pharsight Corp, St. Louis, Mo.).

Oral Glucose Tolerance Tests (OGTT):

CD1 mice were fasted overnight and then administered with certain amount of peptides through s.c. injection (10 μg/mice). After 4 hours, mice were orally administered with 2 g of glucose solution per kg body weight and their tail blood glucose levels were measured before (0 min) and after glucose challenge for 2 to 3 hours.

Synthesis of 6,6'-bis(bromomethyl)-3,3'-bipyridine (Bpy)

6, 6'-dimethyl-3,3'-bipyridine (0.368 g, 2 mmol) was dissolved in 20 mL anhydrous $CCl_4$. N-bromosuccinimide (0.712 g, 4 mmol) and AIBN (20 mg, catalytic amount) were added to the solution. The mixture was refluxed for 5 hours before $CCl_4$ was removed under vacuum. Recrystallization of the crude from DCM afforded the titled compound as a white solid (90 mg, 14% yield): $^1$H NMR (300 MHz, $CDCl_3$) δ 8.80 (d, J=2.1 Hz, 2H), 7.89 (dd, J=8.1 Hz, 2.4 Hz, 2H), 7.56 (d, J=8.1 Hz, 1H), 4.61 (s, 4H); 13C NMR (75 MHz, CDCl3) δ 156.76, 147.96, 135.44, 132.26, 123.62, 33.29; HRMS (EI) calcd for $C_{12}H_{10}Br_2N_2$ 339.9205 [M$^+$], found 339.9206.

Synthesis of p-phenylene-3,3'-bis(allylbromide) (Alk)

To a solution of dimethyl-1,4-phenylenediacrylate (0.5 g, 2.0 mmol) in 10 mL THF at −78° C. was added dropwise DIBAL (1.2 M in toluene, 10 mL), and the mixture was stirred overnight. The reaction was quenched by adding water followed by saturated ammonium chloride before extraction with ethyl acetate. The organic layer was separated, dried over $MgSO_4$, and concentrated under reduced pressure to afford p-phenylene-3,3'-bis(allyl alcohol) as white flakes (330 mg, 85% yield): $^1$H NMR (300 MHz, CDCl3) δ 4.21-4.23 (m, 4H), 6.33-6.40 (m, 2H), 6.56-6.61 (m, 2H), 7.35 (s, 4H). To a solution of p-phenylene-3,3'-bis(allyl alcohol) (15 mg, 0.08 mmol) in 2 mL anhydrous ether at 0° C. was added dropwise $PBr_3$ (6 μL, 0.07 mmol), and the reaction mixture was stirred at 0° C. for 10 min and then at room temperature for 30 min. Dichloromethane (1 mL) was added, and the organic layer was separated, washed with a saturated $NaHCO_3$ solution, dried over anhydrous $Na_2SO_4$, and concentrated under reduced pressure to afford the titled compound (15 mg, 65% yield): $^1$H NMR (300 MHz, CDCl3) δ 4.17-4.19 (m, 4H), 6.37-6.42 (m, 2H), 6.59-6.65 (m, 2H), 7.35 (s, 4H).

Manufacture of bis(bromomethyl)phenazine (Phen)

Phenazine derivative was synthesized through double Buchwald-Hartwig amination reaction as reported. Briefly, a mixture of bromoaniline (200 mg, 0.5 mmol), cesium carbonate (350 mg, 1.0 mmol), Pd(OAc)$_2$ (6.0 mg, 0.025 mmol), and SPhos (20 mg, 0.084 mmol) in 5 mL anhydrous toluene was stirred at 120° C. overnight. The mixture was then diluted with chloroform and filtered through a layer of Celite. The filtrate was concentrated to give bis(methyl) phenazine (60 mg, 54% yield): $^1$H NMR (500 MHz, $CDCl_3$) δ 8.13 (d, J=9.0 Hz, 2H), 8.00 (s, 2H), 7.68 (d, J=9.0 Hz, 2H), 2.67 (s, 6H). A solution of bis(methyl)phenazine (50 mg, 0.24 mmol), NBS (84 mg, 0.48 mmol), and AIBN (8 mg, 0.2 equiv) in 3 mL $CCl_4$ was refluxed overnight. After evaporating the solvent, the residue was subjected to silica gel flash chromatography using 10% ethyl acetate/hexanes as eluent to afford the titled product (15 mg, 20% yield): $^1$H NMR (500 MHz, $CDCl_3$) δ 8.26 (d, J=8.5 Hz, 2H), 8.23 (d, J=2.0 Hz, 2H), 7.91 (dd, J=8.5, 2.0 Hz, 2H), 4.77 (s, 4H).

Example 2

This example provides a description of methods of preparation of examples of crosslinking agents of the present disclosure and characterization of same. Also provided is a description of preparation and characterization of crosslinked OXM analog peptides of the present disclosure. Scheme 1 shows synthesis of an example of a crosslinked OXM analog peptide of the present disclosure. The amino acid sequence of OXM-11ph-1 is given in SEQ ID NO:9).

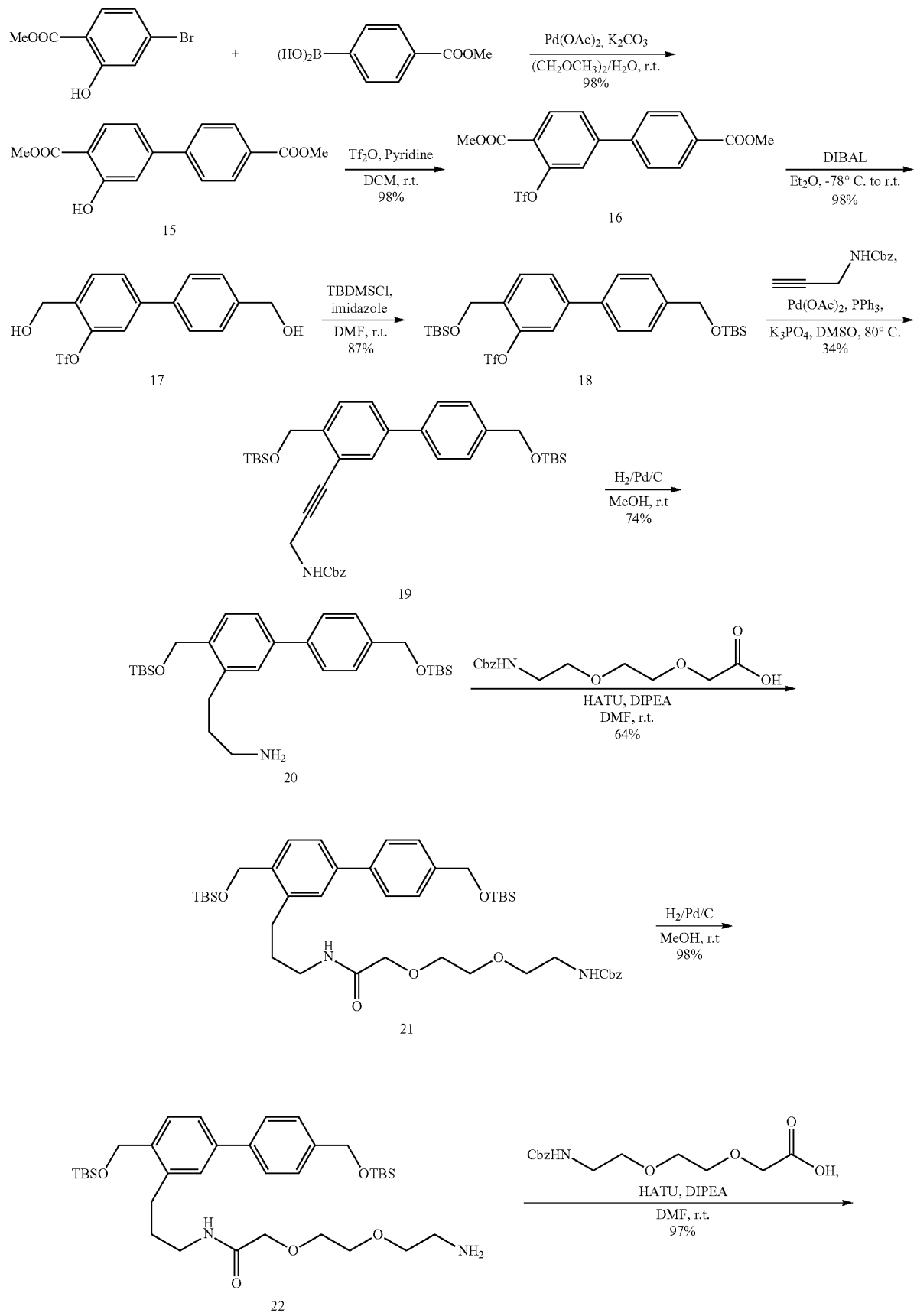

-continued
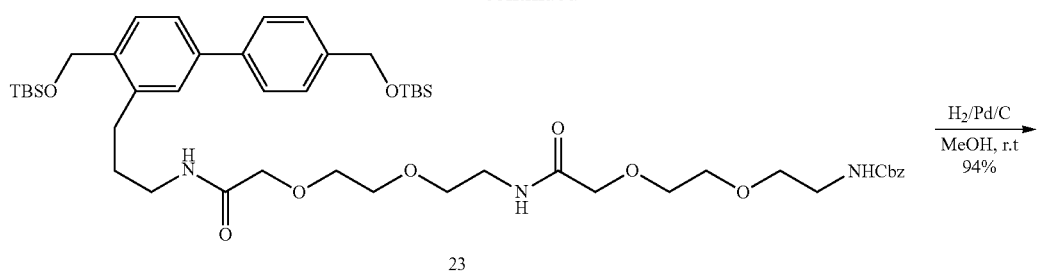
23
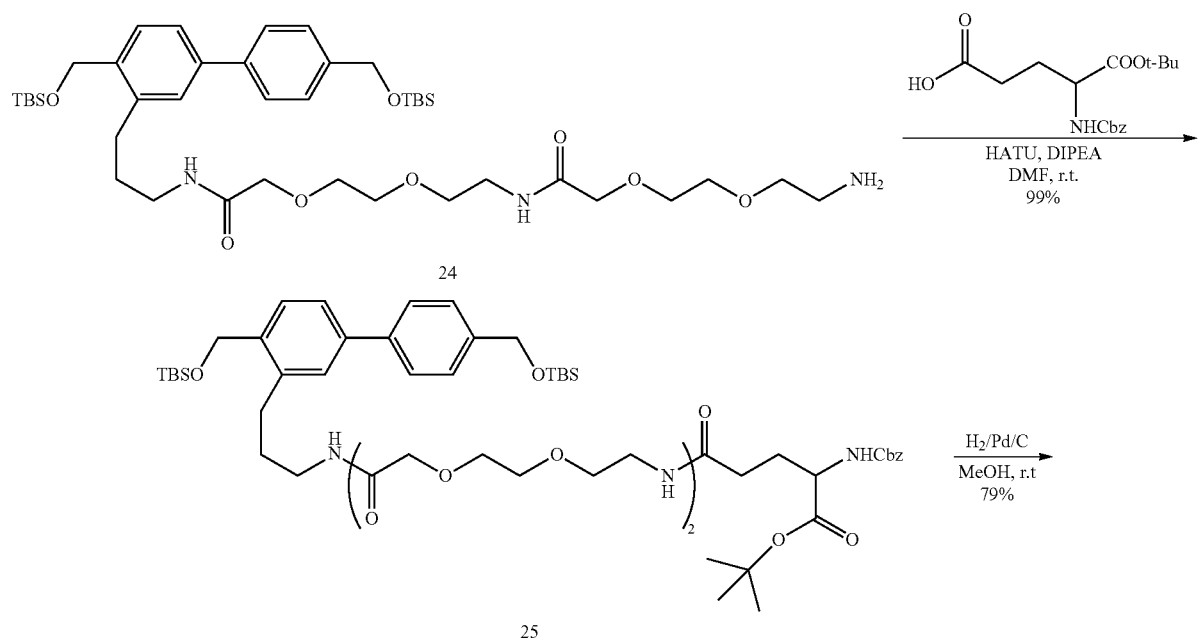
24
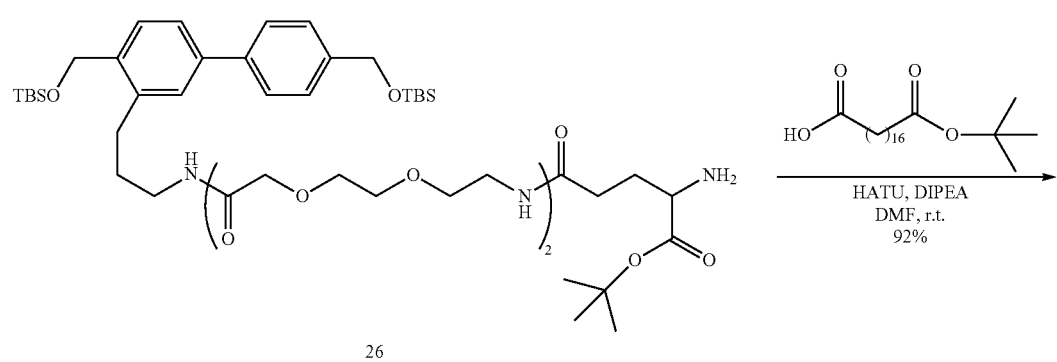
26
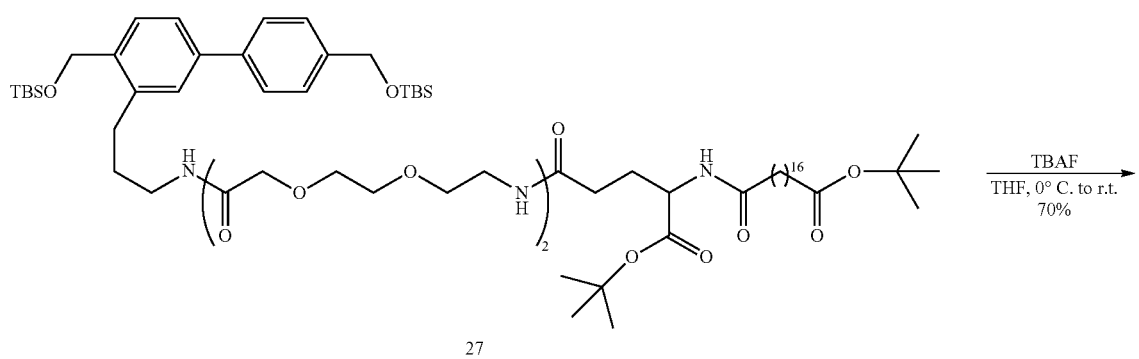
27

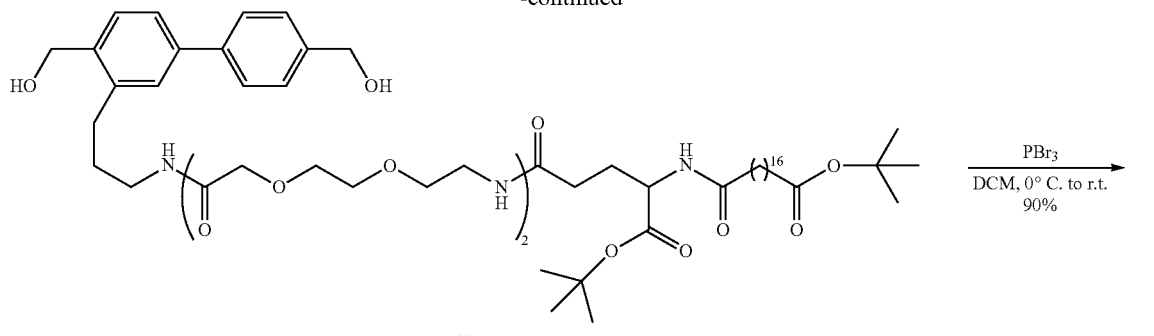

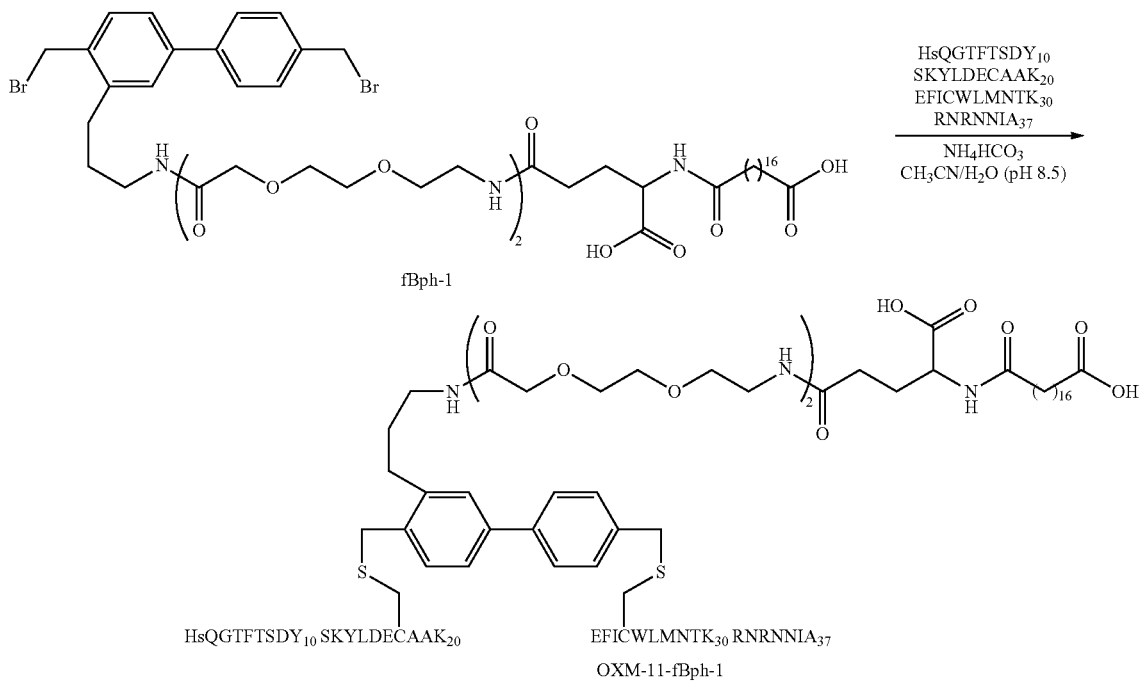

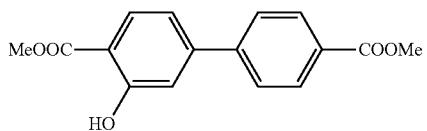

Preparation of dimethyl 3-hydroxy-[1,1'-biphenyl]-4,4'-dicarboxylate (15)

To a solution of methyl 4-bromo-2-hydroxybenzoate (307 mg, 1.3 mmol) in $(CH_3OCH_2)_2/H_2O$ (10 mL, 1:1) was added (4-(methoxycarbonyl)phenyl)boronic acid (287 mg, 1.6 mmol), $Pd(OAc)_2$ (15 mg, 0.07 mmol), $PPh_3$ (17 mg, 0.07 mmol) and $K_2CO_3$ (551 mg, 4 mmol). The mixture was stirred at room temperature under argon protection for 12 h. The solution was neutralized by 1N HCl, diluted with EtOAc, wash with $H_2O$, brine, dried over anhydrous $Na_2SO_4$, filtered and concentrated. The residue was purified by silica gel flash column chromatography (hexane/EtOAc=5:1) to afford compound 15 (363 mg, 98%). Yellow solid; $^1H$ NMR (500 MHz, $CDCl_3$) δ 10.82 (s, 1H), 8.12 (d, J=8.2 Hz, 2H), 7.92 (d, J=8.3 Hz, 1H), 7.68 (d, J=8.2 Hz, 2H), 7.24 (d, J=1.3 Hz, 1H), 7.15 (dd, J=8.3, 1.3 Hz, 1H), 3.98 (s, 3H), 3.95 (s, 3H).

Preparation of dimethyl 3-(((trifluoromethyl)sulfonyl)oxy)-[1,1'-biphenyl]-4,4'-dicarboxylate (16)

To a solution of 15 (440 mg, 1.5 mmol) in dichloromethane (10 mL) was added pyridine (593 mg, 7.5 mmol) and $H_2O$ (650 mg, 2.3 mmol) at 0° C. The mixture was stirred at room temperature for 12 h, then concentrated. The residue was dissolved in EtOAc, washed with 1N HCl, brine, dried over anhydrous $Na_2SO_4$, filtered and concentrated. The residue was purified by silica gel flash column chromatography (hexane/EtOAc=4:1) to afford compound 16 (614 mg, 98%). Colorless oil; $^1H$ NMR (300 MHz, $CDCl_3$) δ 8.22-

8.11 (m, 3H), 7.71 (dd, J=8.2, 1.7 Hz, 1H), 7.68-7.61 (m, 2H), 7.51 (d, J=1.5 Hz, 1H), 4.00 (s, 3H), 3.96 (s, 3H).

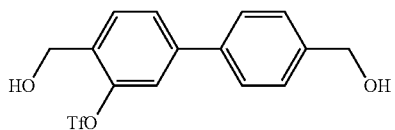

Preparation of 4,4'-bis(hydroxymethyl)-[1,1'-biphenyl]-3-yl trifluoromethanesulfonate (17)

To a solution of 17 (614 mg, 1.5 mmol) in Et₂O (10 mL) was added 1.2 M DIBAL in toluene (5 mL, 6 mmol) at −78° C. The mixture was stirred at room temperature for 3 h. Then 10% potassium sodium tartrate solution was added, stirred for another 1 h. The organic layer was washed with brine, dried over anhydrous Na₂SO₄, filtered and concentrated. The residue was purified by silica gel flash column chromatography (hexane/EtOAc=2:1) to afford compound 17 (530 mg, 99% yield). White solid; ¹H NMR (300 MHz, CDCl₃) δ 7.70-7.52 (m, 2H), 7.60-7.53 (m, 2H), 7.51-7.45 (m, 3H), 4.84 (d, J=5.6 Hz, 2H), 4.77 (d, J=4.8 Hz, 2H).

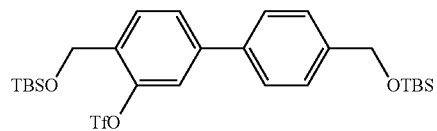

Preparation of 4,4'-bis(((tert-butyldimethylsilyl)oxy)methyl)-[1,1'-biphenyl]-3-yl trifluoromethanesulfonate (18)

To a solution of 17 (532 mg, 1.5 mmol) in DMF (8 mL) was added imidazole (89 mg, 11.8 mmol) and TBDMSCl (888 mg, 5.9 mmol) at 0° C. The mixture was stirred at room temperature for 1 h. Then saturated NH₄Cl was added and extracted with EtOAc. The organic layer was washed with brine, dried over anhydrous Na₂SO₄, filtered and concentrated. The residue was purified by silica gel flash column chromatography (hexane/EtOAc=3:1) to afford compound 4 (754 mg, 87%). Colorless oil; ¹H NMR (300 MHz, CDCl₃) δ 7.69 (d, J=8.1 Hz, 1H), 7.61 (dd, J=8.0, 1.7 Hz, 1H), 7.56-7.48 (m, 2H), 7.44-7.40 (m, 3H), 4.86 (s, 2H), 4.79 (s, 2H), 0.96 (s, 18H), 0.13 (d, J=4.5 Hz, 12H)

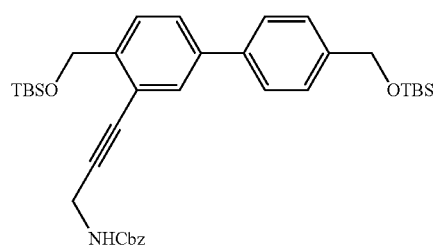

Preparation of benzyl (3-(4,4'-bis(((tert-butyldimethylsilyl)oxy)methyl)-[1,1'-biphenyl]-3-yl)prop-2-yn-1-yl)carbamate (19)

To a solution of 18 (605 mg, 1 mmol) in DMSO (8 mL) was added benzyl prop-2-yn-1-ylcarbamate (291 mg, 1.5 mmo), Pd(OAc)₂ (7 mg, 0.03 mmol), PPh₃ (32 mg, 0.12 mmol), K₃PO4 (255 mg, 1.2 mmol). The mixture was stirred at 80° C. under argon protection for 16 h. Then H₂O was added and extracted with Et₂O. The organic layer was washed with brine, dried over anhydrous Na₂SO₄, filtered and concentrated. The residue was purified by silica gel flash column chromatography (hexane/EtOAc=4:1) to afford compound 19 (200 mg, 34%). Colorless oil; ¹H NMR (500 MHz, CDCl₃) δ 7.61 (s, 1H), 7.57 (s, 2H), 7.53 (d, J=8.1 Hz, 2H), 7.39-7.29 (m, 7H), 5.15 (s, 2H), 5.01 (s, 1H), 4.87 (s, 2H), 4.78 (s, 2H), 4.28 (s, 2H), 0.97 (s, 18H), 0.12 (s, 12H).

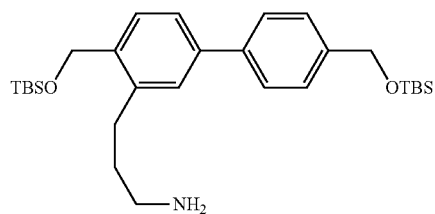

Preparation of 3-(4,4'-bis(((tert-butyldimethylsilyl)oxy)methyl)-[1,1'-biphenyl]-3-yl)propan-1-amine (20)

To a solution of 19 (200 mg, 0.32 mmol) in MeOH (5 mL) was added Pd/C (40 mg, 20%). The mixture was stirred at room temperature under H₂ for 1 h, then filtered and concentrated to afford compound 20 (118 mg, 74% yield). Colorless oil; ¹H NMR (500 MHz, CDCl₃) δ 7.55 (d, J=8.1 Hz, 2H), 7.47 (d, J=7.8 Hz, 1H), 7.42 (d, J=7.5 Hz, 1H), 7.40-7.35 (m, 3H), 4.78 (s, 4H), 2.81 (t, J=7.1 Hz, 2H), 2.71 (t, J=7.8 Hz, 2H), 1.84-1.78 (m, 2H), 0.96 (s, 18H), 0.11 (s, 12H).

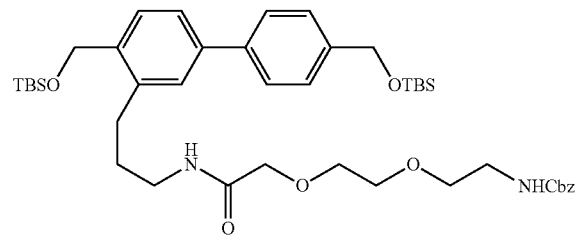

Preparation of benzyl (2-(2-(2-((3-(4,4'-bis(((tert-butyldimethylsilyl)oxy)methyl)-[1,1'-biphenyl]-3-yl)propyl)amino)-2-oxoethoxy)ethoxy)ethyl)carbamate (21)

To a solution of 20 (118 mg, 0.24 mmol) in DMF (3 mL) was added 3-oxo-1-phenyl-2,7,10-trioxa-4-azadodecan-12-oic acid (86 mg, 0.29 mmol), HATU (110 mg, 0.29 mmol) and DIPEA (124 mg, 0.96 mmol). The mixture was stirred at room temperature for 1 h. Then H₂O was added and extracted with EtOAc. The organic layer was washed with brine, dried over anhydrous Na₂SO₄, filtered and concentrated. The residue was purified by silica gel flash column chromatography (hexane/EtOAc=1:2) to afford compound 21 (100 mg, 54% yield). Colorless oil; ¹H NMR (300 MHz, CDCl$_3$) δ 7.55 (d, J=8.1 Hz, 2H), 7.48-7.41 (m, 2H), 7.41-7.35 (m, 3H), 7.34-7.30 (m, 5H), 6.79 (s, 1H), 5.07 (s, 2H), 4.78 (s, 2H), 4.76 (s, 2H), 3.97 (s, 2H), 3.61 (dd, J=11.0, 5.5 Hz, 4H), 3.53 (t, J=5.1 Hz, 2H), 3.36 (t, J=5.8 Hz, 4H), 2.73-2.64 (m, 2H), 0.95 (d, J=3.2 Hz, 19H), 0.12 (s, 12H).

22

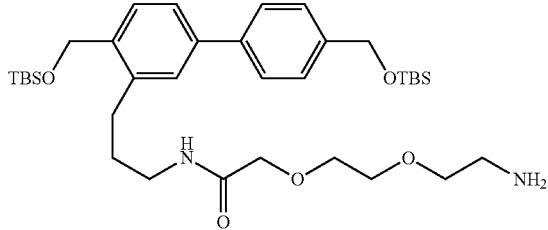

Preparation of 2-(2-(2-aminoethoxy)ethoxy)-N-(3-(4,4'-bis(((tert-butyldimethylsilyl)oxy)methyl)-[1,1'-biphenyl]-3-yl)propyl)acetamide (22)

To a solution of 21 (80 mg, 0.1 mmol) in MeOH (2 mL) was added Pd/C (16 mg, 20%). The mixture was stirred at room temperature under H$_2$ for 1 h, then filtered and concentrated to afford compound 22 (65 mg, 99%). Colorless oil; $^1$H NMR (500 MHz, CDCl$_3$) δ 7.55 (d, J=7.9 Hz, 2H), 7.47 (d, J=7.8 Hz, 1H), 7.43 (d, J=8.0 Hz, 1H), 7.40-7.36 (m, 3H), 6.99 (s, 1H), 4.77 (d, J=7.6 Hz, 4H), 3.99 (s, 2H), 3.67 (d, J=4.2 Hz, 2H), 3.62 (d, J=4.0 Hz, 2H), 3.48 (d, J=4.5 Hz, 2H), 3.39 (q, J=6.8 Hz, 2H), 2.83 (t, J=5.2 Hz, 2H), 2.74-2.66 (m, 2H), 1.96-1.82 (m, 2H), 0.96 (s, 18H), 0.12 (s, 12H).

23

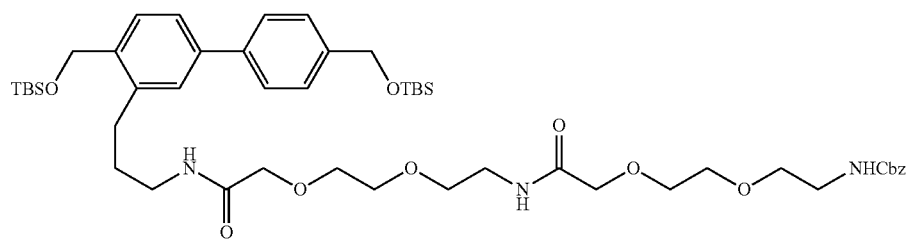

Preparation of benzyl (21-(4,4'-bis(((tert-butyldimethylsilyl)oxy)methyl)-[1,1'-biphenyl]-3-yl)-8,17-dioxo-3,6,12,15-tetraoxa-9,18-diazahenicosyl)carbamate (23)

To a solution of 22 (65 mg, 0.1 mmol) in DMF (2 mL) was added 3-oxo-1-phenyl-2,7,10-trioxa-4-azadodecan-12-oic acid (36 mg, 0.12 mmol), HATU (46 mg, 0.12 mmol) and DIPEA (52 mg, 0.4 mmol). The mixture was stirred at room temperature for 1 h. Then H$_2$O was added and extracted with EtOAc. The organic layer was washed with brine, dried over anhydrous Na$_2$SO$_4$, filtered and concentrated. The residue was purified by silica gel flash column chromatography (DCM/MeOH=15:1) to afford compound 23 (99 mg, 99% yield). Colorless oil; $^1$H NMR (500 MHz, CDCl$_3$) δ 7.55 (d, J=7.9 Hz, 2H), 7.47 (d, J=7.7 Hz, 1H), 7.42 (d, J=7.3 Hz, 1H), 7.38 (d, J=6.7 Hz, 3H), 7.34-7.28 (m, 5H), 7.13 (s, 1H), 6.77 (s, 1H), 5.30 (s, 2H), 5.08 (s, 2H), 4.77 (d, J=8.8 Hz, 4H), 3.95 (s, 4H), 3.60-3.50 (m, 10H), 3.45 (s, 2H), 3.40-3.28 (m, 4H), 2.75-2.62 (m, 2H), 1.93-1.80 (m, 2H), 0.95 (d, J=4.6 Hz, 18H), 0.12 (s, 12H).

24

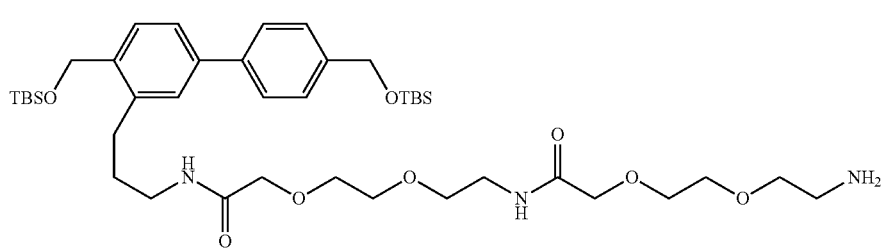

Preparation of 2-(((14-amino-7-oxo-3,9,12-trioxa-6-azatetradecyl)oxy)-N-(3-(4,4'-bis(((tert-butyldimethylsilyl)oxy)methyl)-[1,1'-biphenyl]-3-yl)propyl)acetamide (24)

To a solution of 23 (99 mg, 0.1 mmol) in MeOH (2 mL) was added Pd/C (20 mg, 20%). The mixture was stirred at room temperature under H$_2$ for 1 h, then filtered and concentrated to afford compound 24 (74 mg, 94% yield). Colorless oil; $^1$H NMR (500 MHz, CDCl$_3$) δ 7.55 (d, J=7.9 Hz, 2H), 7.48-7.42 (m, 2H), 7.39-7.35 (m, 3H), 7.19 (s, 1H), 7.01 (s, 1H), 4.77 (d, J=7.3 Hz, 4H), 3.98 (d, J=6.9 Hz, 4H), 3.69-3.53 (m, 10H), 3.53-3.45 (m, 4H), 3.42-3.35 (m, 2H), 2.84 (t, J=5.1 Hz, 2H), 2.71 (t, J=7.9 Hz, 2H), 1.94-1.85 (m, 2H), 0.95 (d, J=3.7 Hz, 18H), 0.12 (s, 12H).

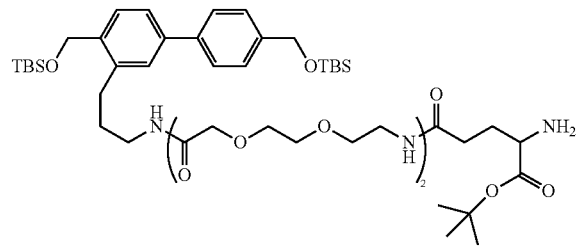

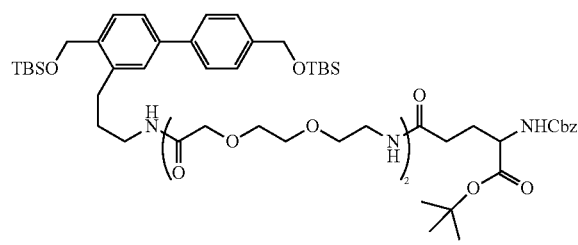

Preparation of tert-butyl 26-(((benzyloxy)carbonyl)amino)-1-(4,4'-bis(((tert-butyldimethylsilyl)oxy)methyl)-[1,1'-biphenyl]-3-yl)-5,14,23-trioxo-7,10,16,19-tetraoxa-4,13,22-triazaheptacosan-27-oate (25)

To a solution of 24 (68 mg, 0.09 mmol) in DMF (1 mL) was added 4-(((benzyloxy)carbonyl)amino)-5-(tert-butoxy)-5-oxopentanoic acid (35 mg, 0.1 mmol), HATU (38 mg, 0.1 mmol) and DIPEA (44 mg, 0.34 mmol). The mixture was stirred at room temperature for 1 h. Then H$_2$O was added and extracted with EtOAc. The organic layer was washed with brine, dried over anhydrous Na$_2$SO$_4$, filtered and concentrated. The residue was purified by silica gel flash column chromatography (DCM/MeOH=15:1) to afford compound 25 (97 mg, 99%). Colorless oil; $^1$H NMR (500 MHz, CDCl$_3$) δ 7.55 (d, J=8.1 Hz, 2H), 7.49-7.40 (m, 2H), 7.40-7.35 (m, 3H), 7.34-7.29 (m, 5H), 7.05 (s, 1H), 6.82 (s, 1H), 6.50 (s, 1H), 5.08 (s, 2H), 4.77 (d, J=8.2 Hz, 4H), 4.22-4.19 (m, 1H), 3.97 (d, J=8.4 Hz, 4H), 3.70-3.29 (m, 20H), 2.71 (t, J=7.9 Hz, 2H), 2.30-2.10 (m, 2H), 1.93-1.88 (m, 2H), 1.56 (s, 9H), 0.95 (d, J=4.4 Hz, 18H), 0.12 (s, 12H).

Preparation of tert-butyl 26-amino-1-(4,4'-bis(((tert-butyldimethylsilyl)oxy)methyl)-[1,1'-biphenyl]-3-yl)-5,14,23-trioxo-7,10,16,19-tetraoxa-4,13,22-triazaheptacosan-27-oate (26)

To a solution of 25 (95 mg, 0.09 mmol) in MeOH (2 mL) was added Pd/C (19 mg, 20%). The mixture was stirred at room temperature under H$_2$ for 1 h, then filtered and concentrated to afford compound 26 (66 mg, 79% yield). Colorless oil; $^1$H NMR (500 MHz, CDCl$_3$) δ 7.57 (d, J=8.0 Hz, 2H), 7.51-7.42 (m, 2H), 7.42-7.33 (m, 3H), 7.08 (s, 1H), 6.86 (s, 1H), 6.60 (s, 1H), 4.79 (d, J=7.5 Hz, 4H), 4.18-4.11 (m, 1H), 4.00 (d, J=9.0 Hz, 4H), 3.71-3.26 (m, 18H), 2.73 (t, J=7.6 Hz, 2H), 2.34 (t, J=7.2 Hz, 2H), 2.16-2.00 (m, 1H), 1.98-1.86 (m, 2H), 1.81-1.75 (m, 1H), 1.46 (s, 9H), 0.97 (d, J=4.0 Hz, 18H), 0.14 (s, 12H).

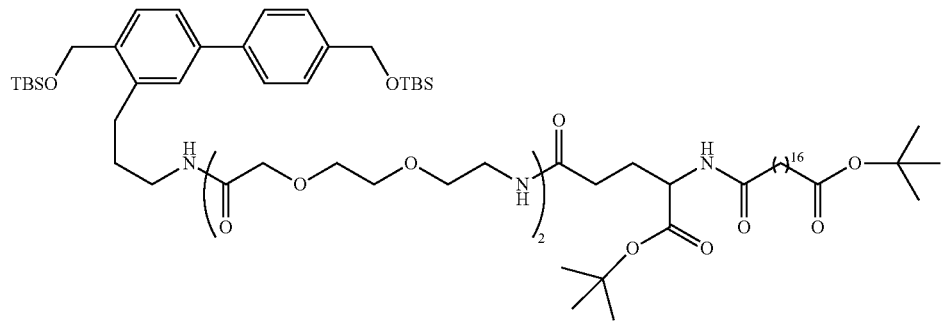

Preparation of tert-butyl 1-(4,4'-bis(((tert-butyldimethylsilyl)oxy)methyl)-[1,1'-biphenyl]-3-yl)-26-(tert-butoxycarbonyl)-5,14,23,28-tetraoxo-7,10,16,19-tetraoxa-4,13,22,27-tetraazapentatetracontan-45-oate (27)

To a solution of 26 (65 mg, 0.07 mmol) in DMF (1 mL) was added 18-(tert-butoxy)-18-oxooctadecanoic acid (30 mg, 0.08 mmol), HATU (30 mg, 0.08 mmol) and DIPEA (26 mg, 0.2 mmol). The mixture was stirred at room temperature for 1 h. Then H$_2$O was added and extracted with EtOAc. The organic layer was washed with brine, dried over anhydrous Na$_2$SO$_4$, filtered and concentrated. The residue was purified by silica gel flash column chromatography (DCM/

MeOH=15:1) to afford compound 27 (82 mg, 92% yield). Colorless oil; $^1$H NMR (500 MHz, CDCl$_3$) δ 7.55 (d, J=8.0 Hz, 2H), 7.49-7.41 (m, 2H), 7.40-7.35 (m, 3H), 7.05 (s, 1H), 6.85 (s, 1H), 6.75 (s, 1H), 6.49 (d, J=7.2 Hz, 1H), 4.77 (d, J=7.6 Hz, 4H), 4.40 (s, 1H), 3.98 (d, J=10.1 Hz, 4H), 3.71-3.31 (m, 20H), 2.72 (t, J=7.8 Hz, 2H), 2.32-2.24 (m, 2H), 2.19 (t, J=7.4 Hz, 2H), 1.97-1.83 (m, 2H), 1.65-1.59 (m, 6H), 1.44 (d, J=4.7 Hz, 18H), 1.37-1.16 (m, 24H), 0.95 (d, J=4.2 Hz, 18H), 0.12 (s, 12H).

Preparation of 1-(4,4'-bis(bromomethyl)-[1,1'-biphenyl]-3-yl)-26-carboxy-5,14,23,28-tetraoxo-7,10,16,19-tetraoxa-4,13,22,27-tetraazapentatetracontan-45-oic acid (fBph-1)

To a solution of 28 (40 mg, 0.036 mmol) in DCM (1 mL) was added PBr$_3$ (49 mg, 0.18 mmol) at 0° C. The mixture was stirred at room temperature for 2 h. Then H$_2$O was added. The organic layer was washed with brine, dried over anhydrous Na$_2$SO$_4$, filtered and concentrated to afford compound fBph-1 (36 mg, 90% yield). White solid; $^1$H NMR (500 MHz, CDCl$_3$) δ 7.55 (d, J=8.0 Hz, 2H), 7.46 (d, J=8.0 Hz, 2H), 7.44-7.37 (m, 3H), 7.17 (s, 1H), 7.12 (s, 1H), 7.04 (s, 1H), 4.59 (s, 2H), 4.55 (s, 2H), 4.52-4.47 (m, 1H), 4.08 (s, 2H), 4.02 (s, 2H), 3.76-3.31 (m, 18H), 2.88-2.78 (m, 2H), 2.53-2.33 (m, 2H), 2.32 (t, J=7.4 Hz, 2H), 2.23 (t, J=7.5 Hz, 2H), 2.18-2.04 (m, 2H), 2.05-1.97 (m, 2H), 1.68-1.55 (m, 4H), 1.28-1.22 (m, 24H).

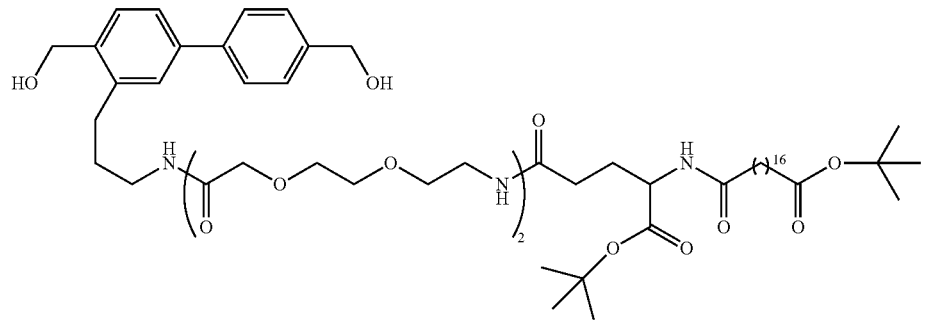

28

Preparation of tert-butyl 1-(4,4'-bis(hydroxymethyl)-[1,1'-biphenyl]-3-yl)-26-(tert-butoxycarbonyl)-5,14,23,28-tetraoxo-7,10,16,19-tetraoxa-4,13,22,27-tetraazapentatetracontan-45-oate (28)

To a solution of 27 (69 mg, 0.05 mmol) in THF (1 mL) was added 1 M TBAF in THF (0.13 mL, 0.13 mmol) at 0° C. The mixture was stirred at room temperature for 2 h. Then H$_2$O was added and extracted with EtOAc. The organic layer was washed with brine, dried over anhydrous Na$_2$SO$_4$, filtered and concentrated. The residue was purified by silica gel flash column chromatography (DCM/MeOH=10:1) to afford compound 28 (40 mg, 70% yield). Colorless oil; $^1$H NMR (500 MHz, CDCl$_3$) δ 7.58 (d, J=8.1 Hz, 2H), 7.49-7.39 (m, 5H), 7.16 (s, 1H), 6.80 (s, 1H), 6.47 (d, J=7.9 Hz, 1H), 4.73 (s, 4H), 4.44-4.33 (m, 1H), 3.92 (d, J=15.1 Hz, 4H), 3.63-3.30 (m, 16H), 2.83 (t, J=7.3 Hz, 2H), 2.29-2.22 (m, 2H), 2.19 (t, J=7.5 Hz, 4H), 2.15-2.04 (m, 1H), 2.00-1.93 (m, 2H), 1.93-1.83 (m, 1H), 1.66-1.51 (m, 6H), 1.45 (d, J=6.2 Hz, 18H), 1.28-1.22 (m, 24H).

Preparation of OXM-11-fBph-1

To a solution of OXM peptide (10 mg, 0.0023 mmol) in 30 mM NH$_4$HCO$_3$ buffer (0.5 mL) was added a solution of fBph-1 (2.5 mg, 0.0023 mmol) in CH$_3$CN (0.5 mL). The mixture was stirred at room temperature for 3 h, then purified using preparative HPLC to afford OXM-11-fBph-1 (2 mg, 17% yield). White solid; ESI-MS m/z calcd For C$_{241}$H$_{366}$N$_{58}$O$_{71}$S$_3$ [M+H]$^+$ 5304.60, found 885.5 [M+6H]$^{6+}$, 1062.3 [M+5H]$^{5+}$, 1327.4 [M+4H]$^{4+}$, 1770.0 [M+3H]$^{3+}$.

fBph-1

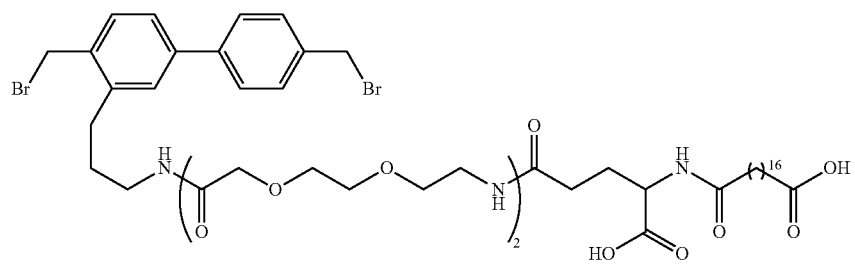

Scheme 2 Synthesis of OXM-11-fBph-2
The amino acid sequence of OXM-11-fBph-2 is given in SEQ ID NO:9:
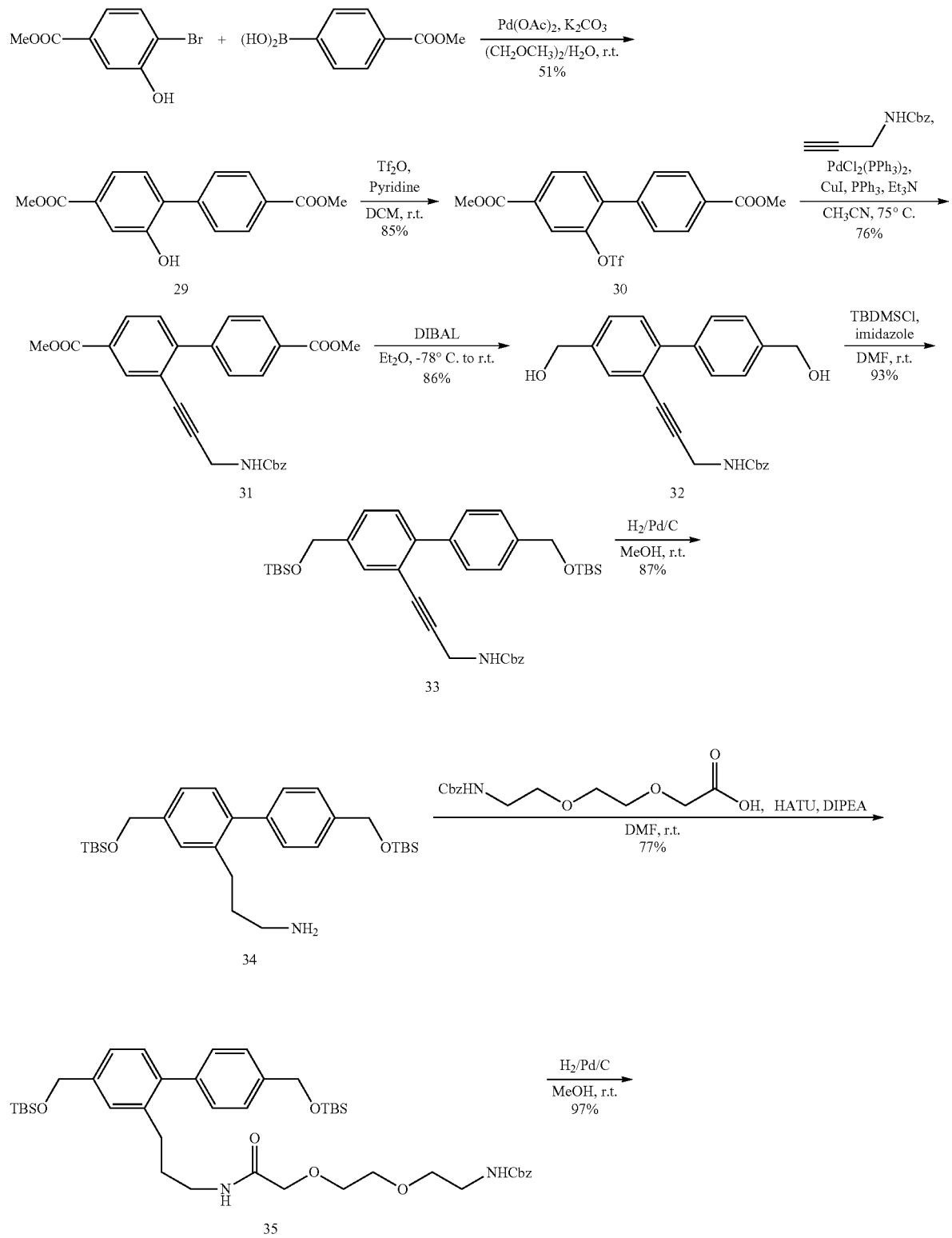

-continued
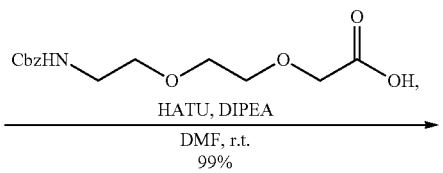
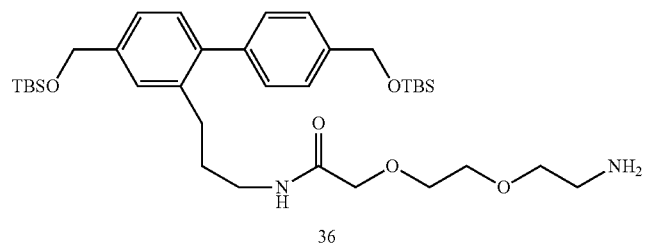
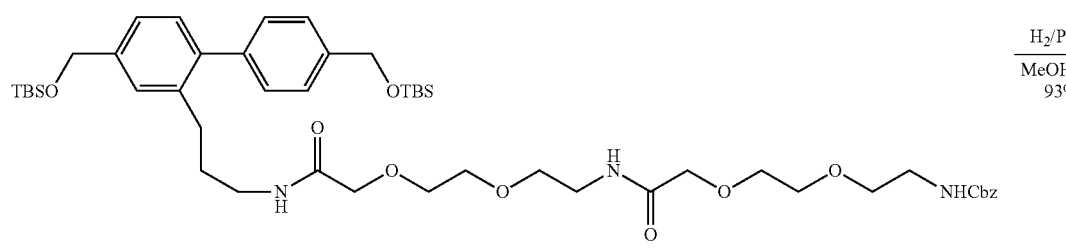
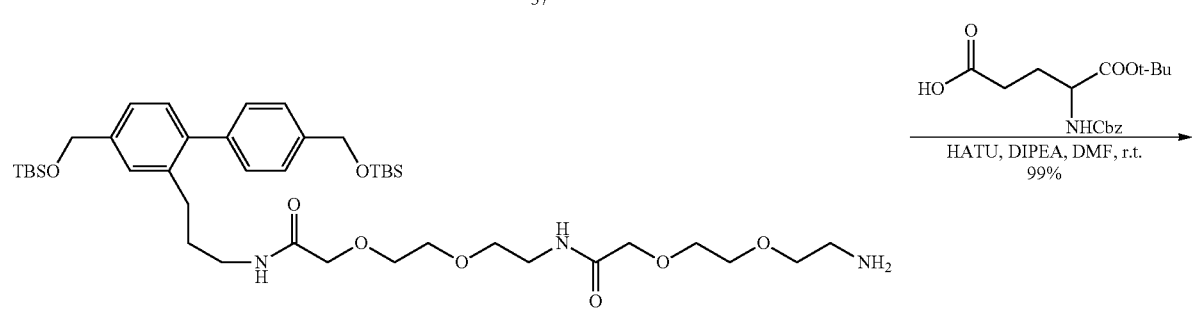
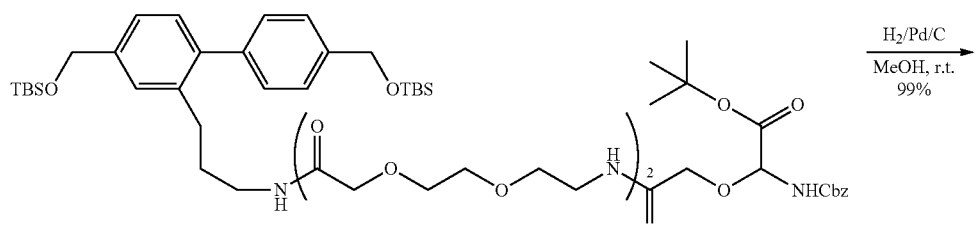
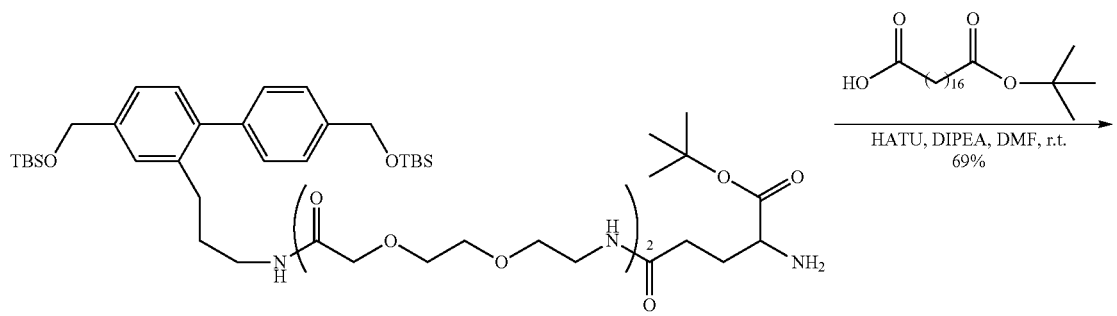

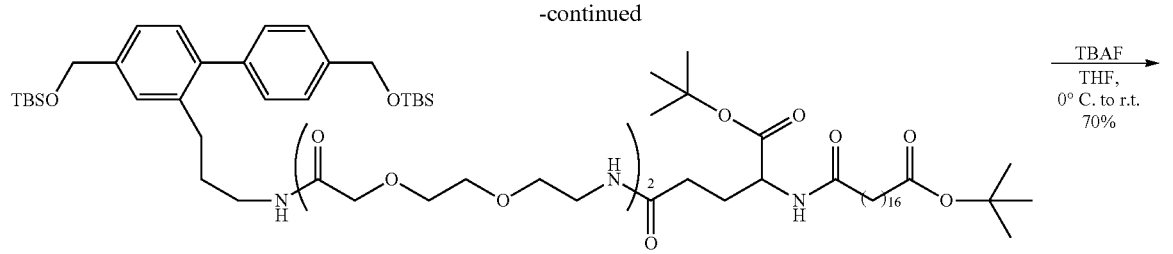

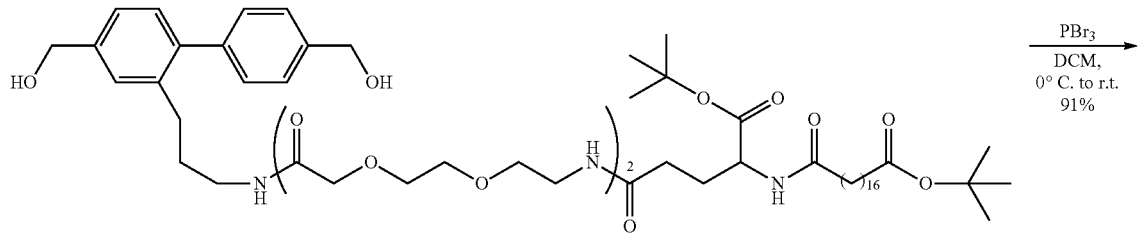

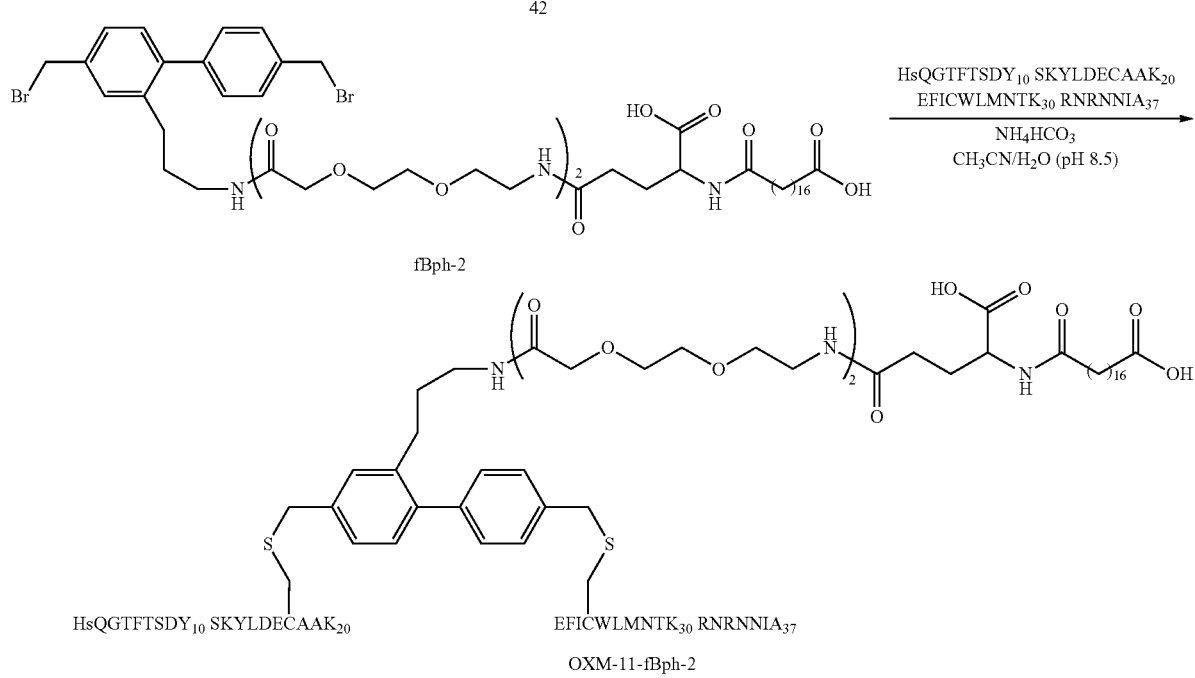

Preparation of dimethyl 2-hydroxy-[1,1'-biphenyl]-4,4'-dicarboxylate (29)

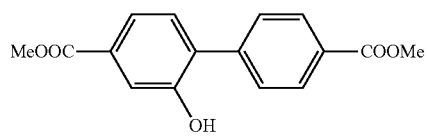

To a solution of methyl 4-bromo-3-hydroxybenzoate (347 mg, 1.5 mmol) in $(CH_3OCH_2)_2/H_2O$ (10 mL, 1:1) was added (4-(methoxycarbonyl)phenyl)boronic acid (324 mg, 1.8 mmol), $Pd(OAc)_2$ (17 mg, 0.08 mmol), $PPh_3$ (20 mg, 0.08 mmol) and $K_2CO_3$ (623 mg, 4.5 mmol). The mixture was stirred at room temperature under argon protection for 12 h. The solution was neutralized by 1N HCl, diluted with EtOAc, wash with $H_2O$, brine, dried over anhydrous $Na_2SO_4$, filtered and concentrated. The residue was purified by silica gel flash column chromatography (hexane/EtOAc=5:1) to afford compound 29 (220 mg, 51% yield). Yellow solid; $^1H$ NMR (500 MHz, $CDCl_3$) δ 8.16 (d, J=8.1 Hz, 2H), 7.69 (dd, J=7.9, 1.1 Hz, 1H), 7.66 (s, 1H), 7.61 (d, J=8.1 Hz, 2H), 7.35 (d, J=7.9 Hz, 1H), 3.96 (s, 3H), 3.94 (s, 3H).

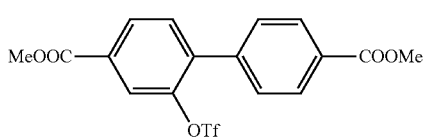

Preparation of dimethyl 2-(((trifluoromethyl)sulfonyl)oxy)-[1,1'-biphenyl]-4,4'-dicarboxylate (30)

To a solution of 29 (300 mg, 1.05 mmol) in dichloromethane (10 mL) was added pyridine (664 mg, 8.4 mmol) and Tf$_2$O (591 mg, 2.1 mmol) at 0° C. The mixture was stirred at room temperature for 12 h, then concentrated. The residue was dissolved in EtOAc, washed with 1N HCl, brine, dried over anhydrous Na$_2$SO$_4$, filtered and concentrated. The residue was purified by silica gel flash column chromatography (hexane/EtOAc=4:1) to afford compound 30 (373 mg, 85%). White solid; $^1$H NMR (300 MHz, CDCl$_3$) δ 8.17-8.03 (m, 3H), 8.06 (s, 1H), 7.60-7.55 (m, 3H), 3.99 (s, 3H), 3.96 (s, 2H).

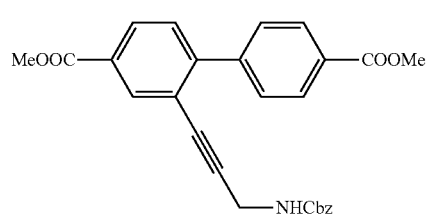

31

Preparation of dimethyl 2-(3-(((benzyloxy)carbonyl)amino)prop-1-yn-1-yl)-[1,1'-biphenyl]-4,4'-dicarboxylate (31)

To a solution of 30 (490 mg, 1.2 mmol) in CH$_3$CN (10 mL) was added benzyl prop-2-yn-1-ylcarbamate (443 mg, 2.3 mmo), PdCl$_2$(PPh$_3$)$_2$ (82 mg, 0.12 mmol), CuI (22 mg, 0.12 mmol), PPh$_3$ (61 mg, 0.23 mmol), Et$_3$N (607 mg, 6 mmol). The mixture was stirred at 75° C. under argon protection for 2 h, then concentrated. The residue was purified by silica gel flash column chromatography (hexane/EtOAc=2:1) to afford compound 31 (357 mg, 67% yield). Yellow solid; $^1$H NMR (500 MHz, CDCl$_3$) δ 8.21 (s, 1H), 8.10 (d, J=7.9 Hz, 2H), 8.04 (d, J=8.1 Hz, 1H), 7.64 (d, J=7.7 Hz, 2H), 7.45 (d, J=8.1 Hz, 1H), 7.39-7.29 (m, 5H), 5.13 (s, 2H), 4.86 (s, 1H), 4.10 (d, J=5.0 Hz, 2H), 3.95 (s, 3H), 3.92 (s, 3H).

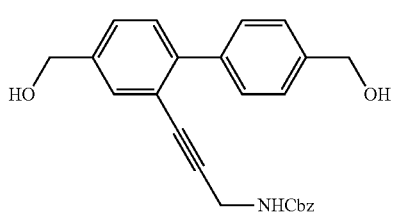

32

Preparation of benzyl (3-(4,4'-bis(hydroxymethyl)-[1,1'-biphenyl]-2-yl)prop-2-yn-1-yl)carbamate (32)

To a solution of 31 (357 mg, 0.78 mmol) in Et$_2$O (10 mL) was added 1.2 M DIBAL in toluene (3.3 mL, 3.9 mmol) at −78° C. The mixture was stirred at room temperature for 3 h. Then 10% potassium sodium tartrate solution was added, stirred for another 1 h. The organic layer was washed with brine, dried over anhydrous Na$_2$SO$_4$, filtered and concentrated. The residue was purified by silica gel flash column chromatography (hexane/EtOAc=1:1) to afford compound 32 (195 mg, 63% yield). White solid; $^1$H NMR (500 MHz, CDCl$_3$) δ 7.57-7.44 (m, 3H), 7.42-7.29 (m, 9H), 5.11 (s, 2H), 4.82 (s, 1H), 4.70 (s, 2H), 4.69 (s, 2H), 4.07 (d, J=4.4 Hz, 2H).

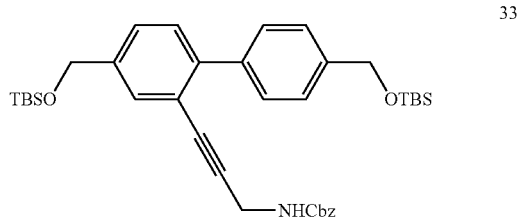 [SMILES: CC(C)(C)[Si](C)(C)OCc1ccc(-c2ccc(CO[Si](C)(C)C(C)(C)C)cc2C#CCNC(=O)OCc2ccccc2)cc1]

33

Preparation of benzyl (3-(4,4'-bis(((tert-butyldimethylsilyl)oxy)methyl)-[1,1'-biphenyl]-2-yl)prop-2-yn-1-yl)carbamate (33)

To a solution of 32 (195 mg, 0.5 mmol) in DMF (5 mL) was added imidazole (267 mg, 3.9 mmol) and TBDMSCl (293 mg, 1.9 mmol) at 0° C. The mixture was stirred at room temperature for 1 h. Then saturated NH$_4$Cl was added and extracted with EtOAc. The organic layer was washed with brine, dried over anhydrous Na$_2$SO$_4$, filtered and concentrated. The residue was purified by silica gel flash column chromatography (hexane/EtOAc=3:1) to afford compound 33 (287 mg, 93% yield). Brown oil; $^1$H NMR (500 MHz, CDCl$_3$) δ 7.51 (d, J=7.6 Hz, 2H), 7.45 (s, 1H), 7.38-7.29 (m, 9H), 5.12 (s, 2H), 4.79 (s, 1H), 4.76 (s, 2H), 4.73 (s, 2H), 4.10 (d, J=4.3 Hz, 2H), 0.96 (d, J=1.1 Hz, 18H), 0.12 (d, J=4.8 Hz, 12H).

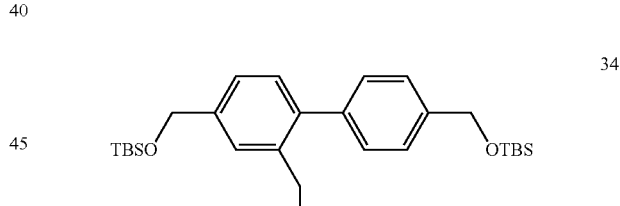

34

Preparation of 3-(4,4'-bis(((tert-butyldimethylsilyl)oxy)methyl)-[1,1'-biphenyl]-2-yl)propan-1-amine (34)

To a solution of 33 (287 mg, 0.46 mmol) in MeOH (5 mL) was added Pd/C (57 mg, 20%). The mixture was stirred at room temperature under H$_2$ for 1 h, then filtered and concentrated to afford compound 34 (200 mg, 87%). Brown oil; $^1$H NMR (500 MHz, CDCl$_3$) δ 7.35 (d, J=7.7 Hz, 2H), 7.29-7.22 (m, 3H), 7.17 (q, J=7.9 Hz, 2H), 4.80 (s, 2H), 4.76 (s, 2H), 2.65-2.58 (m, 2H), 2.56 (t, J=6.9 Hz, 2H), 1.65-1.54 (m, 2H), 0.96 (s, 18H), 0.13 (s, 12H).

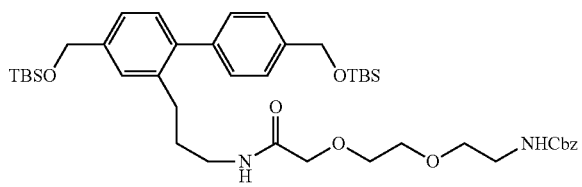

Preparation of benzyl (2-(2-(2-((3-(4,4'-bis(((tert-butyldimethylsilyl)oxy)methyl)-[1,1'-biphenyl]-2-yl)propyl)amino)-2-oxoethoxy)ethoxy)ethyl)carbamate (35)

To a solution of 34 (200 mg, 0.4 mmol) in DMF (3 mL) was added 3-oxo-1-phenyl-2,7,10-trioxa-4-azadodecan-12-oic acid (120 mg, 0.4 mmol), HATU (183 mg, 0.48 mmol) and DIPEA (207 mg, 1.6 mmol). The mixture was stirred at room temperature for 1 h. Then H$_2$O was added and extracted with EtOAc. The organic layer was washed with brine, dried over anhydrous Na$_2$SO$_4$, filtered and concentrated. The residue was purified by silica gel flash column chromatography (hexane/EtOAc=1:2) to afford compound 35 (240 mg, 77% yield). Yellow oil; $^1$H NMR (500 MHz, CDCl$_3$) δ 7.37-7.28 (m, 5H), 7.25-7.17 (m, 6H), 7.15 (d, J=8.1 Hz, 1H), 6.60 (s, 1H), 5.07 (s, 2H), 4.78 (s, 2H), 4.75 (s, 2H), 3.90 (s, 2H), 3.61-3.53 (m, 2H), 3.53-3.43 (m, 2H), 3.39-3.29 (m, 2H), 3.18-3.08 (m, 2H), 2.66-2.56 (m, 2H), 1.72-1.60 (m, 2H), 0.96 (d, J=3.0 Hz, 18H), 0.13 (d, J=3.4 Hz, 12H).

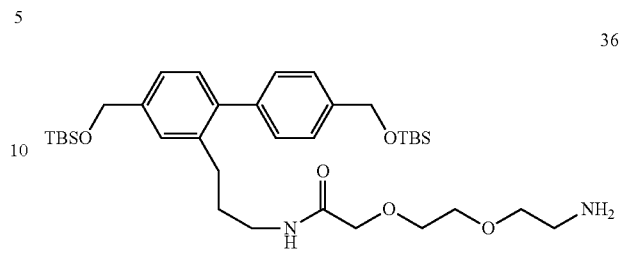

Preparation of 2-(2-(2-aminoethoxy)ethoxy)-N-(3-(4,4'-bis(((tert-butyldimethylsilyl)oxy)methyl)-[1,1'-biphenyl]-2-yl)propyl)acetamide (36)

To a solution of 35 (240 mg, 0.31 mmol) in MeOH (5 mL) was added Pd/C (48 mg, 20%). The mixture was stirred at room temperature under H$_2$ for 1 h, then filtered and concentrated to afford compound 36 (193 mg, 97% yield). Colorless oil; $^1$H NMR (500 MHz, CDCl$_3$) δ 7.35 (d, J=7.8 Hz, 2H), 7.28-7.22 (m, 2H), 7.20 (d, J=9.7 Hz, 2H), 7.15 (d, J=7.6 Hz, 1H), 6.83 (s, 1H), 4.79 (s, 2H), 4.76 (s, 2H), 3.92 (s, 2H), 3.59 (s, 4H), 3.48 (d, J=5.0 Hz, 2H), 3.17 (q, J=6.7 Hz, 2H), 2.82 (t, J=5.2 Hz, 2H), 2.66-2.58 (m, 2H), 1.73-1.65 (m, 2H), 0.97 (d, J=3.4 Hz, 18H), 0.13 (d, J=3.8 Hz, 12H).

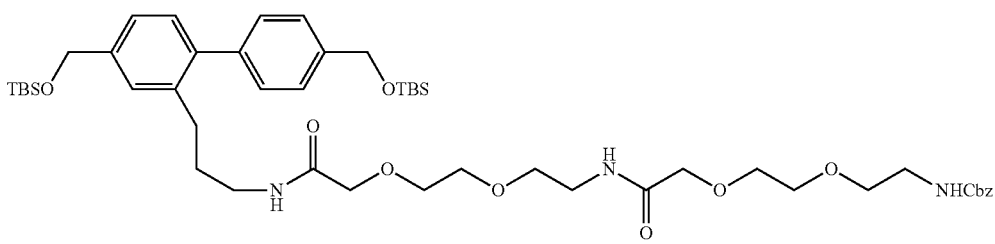

Preparation of benzyl (21-(4,4'-bis(((tert-butyldimethylsdyl)oxy)methyl)-[1,1'-biphenyl]-2-yl)-8,17-dioxo-3,6,12,15-tetraoxa-9,18-diazahenicosyl)carbamate (37)

To a solution of 36 (95 mg, 0.15 mmol) in DMF (2 mL) was added 3-oxo-1-phenyl-2,7,10-trioxa-4-azadodecan-12-oic acid (53 mg, 0.18 mmol), HATU (68 mg, 0.18 mmol) and DIPEA (78 mg, 0.6 mmol). The mixture was stirred at room temperature for 1 h. Then H$_2$O was added and extracted with EtOAc. The organic layer was washed with brine, dried over anhydrous Na$_2$SO$_4$, filtered and concentrated. The residue was purified by silica gel flash column chromatography (DCM/MeOH=15:1) to afford compound 37 (151 mg, 99% yield). Yellow oil; $^1$H NMR (500 MHz, CDCl$_3$) δ 7.38-7.27 (m, 6H), 7.23 (d, J=8.0 Hz, 2H), 7.22-7.17 (m, 2H), 7.15 (d, J=8.2 Hz, 2H), 6.59 (s, 1H), 5.08 (s, 2H), 4.78 (s, 2H), 4.75 (s, 2H), 3.95 (s, 2H), 3.88 (s, 2H), 3.68-3.32 (m, 16H), 3.15 (q, J=6.8 Hz, 2H), 2.67-2.55 (m, 2H), 1.73-1.62 (m, 2H), 0.96 (d, J=3.3 Hz, 18H), 0.13 (d, J=3.6 Hz, 12H).

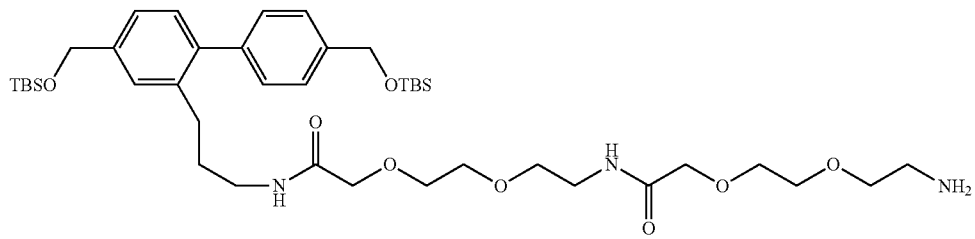

38

Preparation of 2-((14-amino-7-oxo-3,9,12-trioxa-6-azatetradecyl)oxy)-N-(3-(4,4'-bis(((tert-butyldimethylsdyl)oxy)methyl)-[1,1'-biphenyl]-2-yl)propyl)acetamide (38)

To a solution of 37 (139 mg, 0.15 mmol) in MeOH (2 mL) was added Pd/C (30 mg, 20%). The mixture was stirred at room temperature under $H_2$ for 1 h, then filtered and concentrated to afford compound 38 (110 mg, 93%). Colorless oil; $^1$H NMR (500 MHz, CDCl$_3$) δ 7.35 (d, J=7.8 Hz, 2H), 7.24 (d, J=7.9 Hz, 2H), 7.20 (d, J=7.9 Hz, 2H), 7.15 (d, J=7.6 Hz, 1H), 6.81 (s, 1H), 4.79 (s, 2H), 4.76 (s, 2H), 3.98 (s, 2H), 3.92 (s, 2H), 3.66-3.43 (m, 14H), 3.17 (q, J=6.6 Hz, 2H), 2.85 (t, J=5.1 Hz, 2H), 2.68-2.58 (m, 2H), 1.75-1.66 (m, 2H), 0.96 (d, J=3.4 Hz, 18H), 0.13 (d, J=3.9 Hz, 12H).

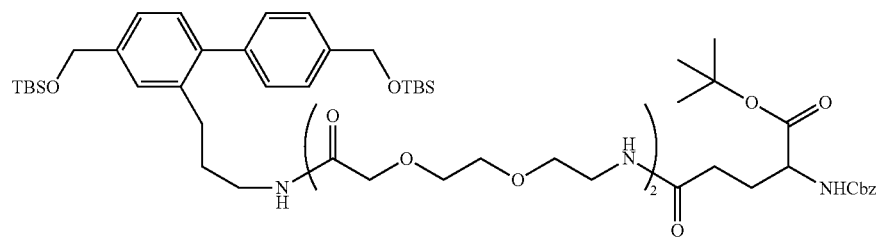

39

Preparation of tert-butyl 26-(((benzyloxy)carbonyl)amino)-1-(4,4'-bis(((tert-butyldimethylsilyl)oxy)methyl)-[1,1'-biphenyl]-2-yl)-5,14,23-trioxo-7,10,16,19-tetraoxa-4,13,22-triazaheptacosan-27-oate (39)

To a solution of 38 (110 mg, 0.14 mmol) in DMF (2 mL) was added 4-(((benzyloxy)carbonyl)amino)-5-(tert-butoxy)-5-oxopentanoic acid (56 mg, 0.17 mmol), HATU (65 mg, 0.17 mmol) and DIPEA (72 mg, 0.56 mmol). The mixture was stirred at room temperature for 1 h. Then H$_2$O was added and extracted with EtOAc. The organic layer was washed with brine, dried over anhydrous Na$_2$SO$_4$, filtered and concentrated. The residue was purified by silica gel flash column chromatography (DCM/MeOH=15:1) to afford compound 39 (176 mg, 99%). Yellow oil; $^1$H NMR (500 MHz, CDCl$_3$) δ 7.38-7.28 (m, 7H), 7.24 (d, J=7.9 Hz, 2H), 7.23-7.19 (m, 2H), 7.15 (d, J=8.2 Hz, 1H), 7.05 (s, 1H), 6.64 (s, 1H), 6.55 (s, 1H), 5.08 (s, 2H), 4.79 (s, 2H), 4.75 (s, 2H), 4.24-4.16 (m, 1H), 3.97 (s, 2H), 3.91 (s, 2H), 3.68-3.34 (m, 18H), 3.15 (t, J=6.6 Hz, 2H), 2.68-2.55 (m, 2H), 2.33-2.23 (m, 2H), 2.22-2.11 (m, 1H), 2.00-1.87 (m, 1H), 1.68 (s, 9H), 0.96 (d, J=3.6 Hz, 18H), 0.13 (d, J=4.1 Hz, 12H).

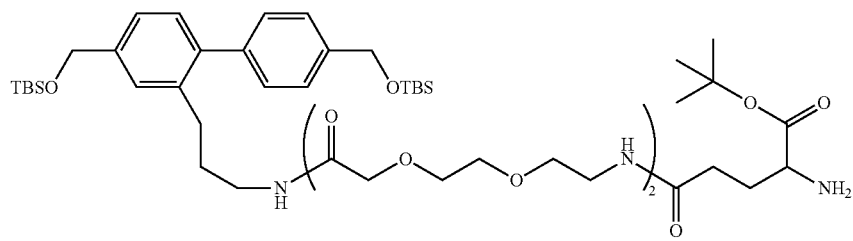

40

Preparation of tert-butyl 26-amino-1-(4,4'-bis(((tert-butyldimethylsilyl)oxy)methyl)-[1,1'-biphenyl]-2-yl)-5,14,23-trioxo-7,10,16,19-tetraoxa-4,13,22-triazaheptacosan-27-oate (40)

To a solution of 39 (155 mg, 0.14 mmol) in MeOH (2 mL) was added Pd/C (31 mg, 20%). The mixture was stirred at room temperature under H₂ for 1 h, then filtered and concentrated to afford compound 40 (137 mg, 99% yield). Colorless oil; $^1$H NMR (500 MHz, CDCl$_3$) δ 7.35 (d, J=7.8 Hz, 2H), 7.24 (d, J=7.9 Hz, 2H), 7.21 (d, J=7.2 Hz, 2H), 7.15 (d, J=8.1 Hz, 1H), 7.09 (s, 1H), 6.66 (s, 1H), 4.79 (s, 2H), 4.76 (s, 2H), 4.16-4.09 (m, 1H), 3.98 (s, 2H), 3.93 (s, 2H), 3.68-3.37 (m, 18H), 3.21-3.11 (m, 2H), 2.63 (t, J=7.7 Hz, 2H), 2.33 (t, J=7.5 Hz, 2H), 2.24-2.03 (m, 2H), 1.47 (s, 9H), 0.96 (d, J=3.5 Hz, 18H), 0.13 (d, J=4.1 Hz, 12H).

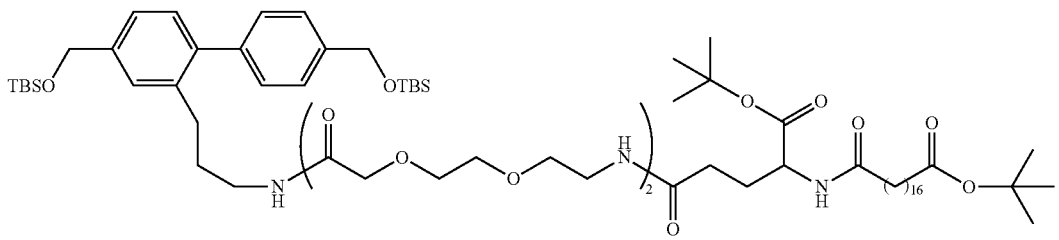

41

Preparation of tert-butyl 1-(4,4'-bis(((tert-butyldimethylsilyl)oxy)methyl)-[1,1'-biphenyl]-2-yl)-26-(tert-butoxycarbonyl)-5,14,23,28-tetraoxo-7,10,16,19-tetraoxa-4,13,22,27-tetraazapentatetracontan-45-oate (41)

To a solution of 40 (137 mg, 0.14 mmol) in DMF (2 mL) was added 18-(tert-butoxy)-18-oxooctadecanoic acid (62 mg, 0.17 mmol), HATU (65 mg, 0.17 mmol) and DIPEA (72 mg, 0.56 mmol). The mixture was stirred at room temperature for 1 h. Then H₂O was added and extracted with EtOAc. The organic layer was washed with brine, dried over anhydrous Na₂SO₄, filtered and concentrated. The residue was purified by silica gel flash column chromatography (DCM/MeOH=15:1) to afford compound 41 (128 mg, 69%). Yellow oil; $^1$H NMR (500 MHz, CDCl$_3$) δ 7.53 (d, J=8.2 Hz, 2H), 7.50-7.42 (m, 2H), 7.41-7.36 (m, 3H), 7.02 (s, 1H), 6.88 (s, 1H), 6.74 (s, 1H), 6.49 (d, J=7.2 Hz, 1H), 4.77 (d, J=7.6 Hz, 4H), 4.45-4.35 (m, 1H), 3.99 (d, J=10.2 Hz, 4H), 3.81-3.42 (m, 20H), 2.74 (t, J=7.8 Hz, 2H), 2.30-2.20 (m, 2H), 2.22 (t, J=7.4 Hz, 2H), 1.95-1.80 (m, 2H), 1.65-1.55 (m, 6H), 1.44 (d, J=4.7 Hz, 18H), 1.36-1.17 (m, 24H), 0.97 (d, J=4.2 Hz, 18H), 0.13 (s, 12H).

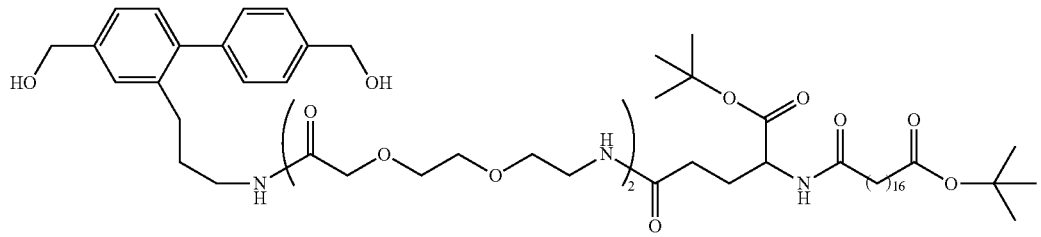

42

Preparation of tert-butyl 1-(4,4'-bis(hydroxymethyl)-[1,1'-biphenyl]-2-yl)-26-(tert-butoxycarbonyl)-5,14,23,28-tetraoxo-7,10,16,19-tetraoxa-4,13,22,27-tetraazapentatetracontan-45-oate (42)

To a solution of 41 (128 mg, 0.1 mmol) in THF (2 mL) was added 1 M TBAF in THF (0.24 mL, 0.24 mmol) at 0° C. The mixture was stirred at room temperature for 2 h. Then H$_2$O was added and extracted with EtOAc. The organic layer was washed with brine, dried over anhydrous Na$_2$SO$_4$, filtered and concentrated. The residue was purified by silica gel flash column chromatography (DCM/MeOH=10:1) to afford compound 42 (64 mg, 70% yield). Colorless oil; $^1$H NMR (500 MHz, CDCl$_3$) δ 7.41 (d, J=7.8 Hz, 2H), 7.31 (s, 1H), 7.28-7.25 (m, 1H), 7.22 (d, J=8.2 Hz, 1H), 7.18 (d, J=7.8 Hz, 2H), 6.92 (s, 1H), 6.78 (s, 1H), 6.52 (d, J=7.6 Hz, 1H), 4.74 (s, 2H), 4.70 (s, 2H), 4.43-4.26 (m, 1H), 3.90 (d, J=2.2 Hz, 4H), 3.64-3.37 (m, 16H), 3.15 (q, J=6.8 Hz, 2H), 2.93 (s, 1H), 2.65 (t, J=7.7 Hz, 2H), 2.26 (dd, J=12.8, 6.9 Hz, 2H), 2.19 (t, J=7.6 Hz, 4H), 2.13 (d, J=6.8 Hz, 1H), 1.97-1.84 (m, 1H), 1.72-1.52 (m, 6H), 1.45 (d, J=7.4 Hz, 18H), 1.34-1.18 (m, 24H).

fBph-2

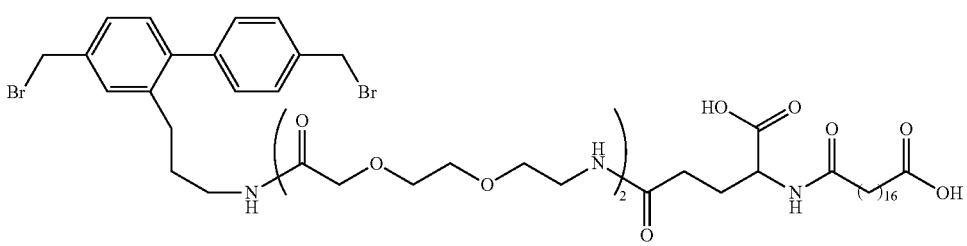

Preparation of 1-(4,4'-bis(bromomethyl)-[1,1'-biphenyl]-2-yl)-26-carboxy-5,14,23,28-tetraoxo-7,10,16,19-tetraoxa-4,13,22,27-tetraazapentatetracontan-45-oic acid (fBph-2)

To a solution of 42 (55 mg, 0.05 mmol) in DCM (2 mL) was added PBr$_3$ (68 mg, 0.25 mmol) at 0° C. The mixture was stirred at room temperature for 2 h. Then H$_2$O was added. The organic layer was washed with brine, dried over anhydrous Na$_2$SO$_4$, filtered and concentrated to afford compound fBph-2 (50 mg, 91%). White Solid; $^1$H NMR (500 MHz, CDCl$_3$) δ 7.44 (d, J=7.9 Hz, 2H), 7.32 (s, 1H), 7.30-7.18 (m, 3H), 7.15 (d, J=7.8 Hz, 1H), 6.85 (s, 1H), 4.56 (s, 2H), 4.52 (s, 2H), 4.50-4.44 (m, 1H), 4.02 (s, 2H), 3.99 (s, 2H), 3.71-3.34 (m, 16H), 3.19 (q, J=6.5 Hz, 2H), 2.66-2.56 (m, 2H), 2.53-2.37 (m, 2H), 2.32 (t, J=7.4 Hz, 2H), 2.25 (t, J=7.5 Hz, 2H), 2.22-2.10 (m, 1H), 2.10-1.99 (m, 1H), 1.76-1.67 (m, 2H), 1.67-1.53 (m, 4H), 1.36-1.16 (m, 24H).

Preparation of OXM-11-fBph-2

To a solution of OXM peptide (10 mg, 0.0023 mmol) in 30 mM NH$_4$HCO$_3$ buffer (0.5 mL) was added a solution of fBph-1 (2.5 mg, 0.0023 mmol) in CH$_3$CN (0.5 mL). The mixture was stirred at room temperature for 3 h, then purified using preparative HPLC to afford OXM-11-fBph-2 (2 mg, 17% yield). White solid; ESI-MS m/z calcd For $C_{241}H_{366}N_{58}O_{71}S_3$ [M+H]$^+$ 5304.60, found 885.5 [M+6H]$^{6+}$, 1062.3 [M+5H]$^{5+}$, 1327.6 [M+4H]$^{4+}$, 1769.9 [M+3H]$^{3+}$.

In vitro activity of OXM-11-Bph, OXM-11-Bpy, OXM-11-fBph-1, and OXM-11-fBph-2 were tested using the same procedure as described in Example 1 (FIG. 6).

Although the present disclosure has been described with respect to one or more particular embodiments and/or examples, it will be understood that other embodiments and/or examples of the present disclosure may be made without departing from the scope of the present disclosure.

The invention claimed is:

1. A crosslinked peptide having the following sequence: HSQGTFTSDYSKYLDSRRAQDFVQWLMNTKRN-RNNIA (SEQ ID NO:1), or a variant thereof having at least 65% homology with SEQ ID NO:1, wherein a first amino acid at position i and a second amino acid at position i+7 are replaced independently by L-cysteine or D-cysteine, i can be at any position from and including number 7 to number 30, the crosslinked peptide is crosslinked with a crosslinking moiety between the cysteines at i and i+7 of the same peptide molecule, and the crosslinking moiety is selected from the group consisting of:

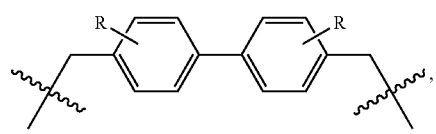

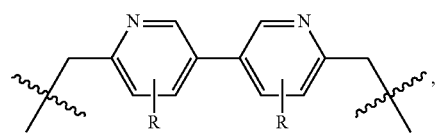

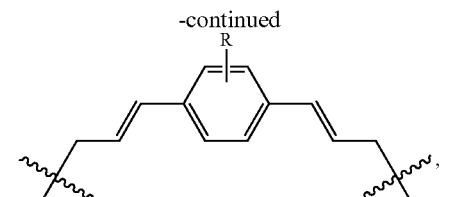

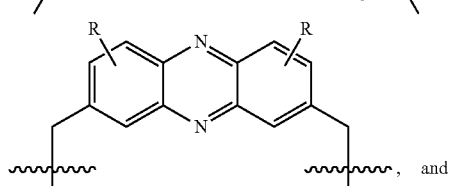, and wherein R at each occurrence on the crosslinking moiety is independently an H, a polyethylene glycol (PEG) group, a lipid group, or a PEG spacer moiety functionalized with a fatty diacid group.

2. The crosslinked peptide of claim 1, wherein i is at position number 17 or number 21.

3. The crosslinked peptide of claim 1, wherein the serine at position 2 is D-serine.

4. The crosslinked peptide of claim 1, wherein the peptide is conjugated with at least one polyethylene glycol group and/or at least one lipid group.

5. The crosslinked peptide of claim 1, wherein the amino acids at positions i+2 to i+6 have a sequence selected from the group consisting of:
RAQDFV (SEQ ID NO:3), AAKEFI (SEQ ID NO:4), AVRLFI (SEQ ID NO:5), and a sequence having at least 80% homology with SEQ ID NO:3, SEQ ID NO:4, or SEQ ID NO:5.

6. The crosslinked peptide of claim 1, wherein the peptide has the following structure:
HsQGTFTSDYSKYLDECAAKEFICWLMNTKRNRN-NIA (SEQ ID NO:11).

7. The crosslinked peptide of claim 6, wherein the crosslinking moiety is selected from the group consisting of:

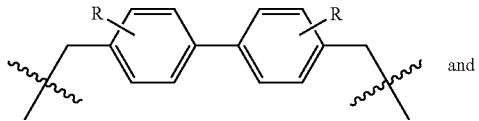 and

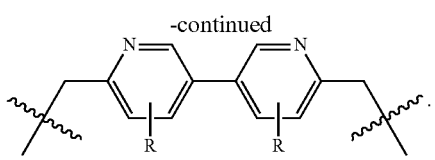.

8. The crosslinked peptide of claim 7, wherein R at each occurrence on the crosslinking moiety is an H.

9. A fusion protein comprising a crosslinked peptide of claim 1, a peptide spacer, and a protein.

10. A composition comprising one or more crosslinked peptide of claim 1 and/or one or more fusion protein of claim 9 and a pharmaceutically acceptable carrier.

11. A method of lowering blood glucose level in an individual in need of treatment comprising administering a composition of claim 10 to the individual,
wherein the administration results in a lowered blood glucose level.

12. A method of inducing weight loss of an individual in need of treatment comprising administering a composition of claim 10 to the individual,
wherein the administration results in a lowered blood glucose level.

* * * * *